(12) United States Patent
Kroeger-Lui

(10) Patent No.: US 10,317,655 B2  
(45) Date of Patent: Jun. 11, 2019

(54) MICROSCOPE FOR MOLECULAR SPECTROSCOPIC ANALYSIS

(71) Applicant: Baden-Wuerttemberg Stiftung gGmbH, Stuttgart (DE)

(72) Inventor: Niels Kroeger-Lui, Kaiserslautern (DE)

(73) Assignee: Baden-Wuerttemberg Stiftung gGmbH, Stuttgart (DE)

( * ) Notice: Subject to any disclaimer, the term of this patent is extended or adjusted under 35 U.S.C. 154(b) by 30 days.

(21) Appl. No.: 15/572,111

(22) PCT Filed: May 6, 2016

(86) PCT No.: PCT/EP2016/060230  
§ 371 (c)(1),  
(2) Date: Nov. 6, 2017

(87) PCT Pub. No.: WO2016/177897  
PCT Pub. Date: Nov. 10, 2016

(65) Prior Publication Data  
US 2018/0157019 A1     Jun. 7, 2018

(30) Foreign Application Priority Data  
May 7, 2015   (DE) .................. 10 2015 107 148

(51) Int. Cl.  
*G01J 3/40* (2006.01)  
*G02B 21/00* (2006.01)  
(Continued)

(52) U.S. Cl.  
CPC ........ *G02B 21/0004* (2013.01); *G01J 3/0205* (2013.01); *G01J 3/2803* (2013.01);  
(Continued)

(58) Field of Classification Search  
CPC ....... G01J 3/02; G01J 3/28; G01J 3/42; G02B 21/00; G02B 21/06; G02B 21/36;  
(Continued)

(56) References Cited

U.S. PATENT DOCUMENTS

2008/0210873 A1    9/2008  Itsuji  
2012/0026311 A1*   2/2012  Ouchi .................. G02B 21/06  
                                                             348/79  
2012/0122084 A1    5/2012  Wagner et al.

OTHER PUBLICATIONS

Fuchs, et al., "Imaging stand-off detection of explosives using tunable MIR quantum cascade lasers", Proc of SPIE 7608, 760809-760809-7 (2010).  
(Continued)

*Primary Examiner* — Abdullahi Nur  
(74) *Attorney, Agent, or Firm* — Viksnins Harris Padys Malen LLP

(57) ABSTRACT

The invention relates to a microscope for the molecular spectroscopic analysis of a sample (2), having a beam path having at least one quantum cascade laser (QCL) (3) which emits an infrared (IR) radiation, a phase modulator (5) which is arranged between the QCL (3) and the sample (2), at least one optical element (6) which is arranged between the phase modulator (5) and the sample (2) and a sensor (4) which detects an IR radiation which is transmitted and/or reflected by the sample (2). The invention relates further to a method for the molecular spectroscopic analysis of a sample (2) comprising the steps of irradiating the sample (2) with an infrared (IR) radiation by means of a quantum cascade laser (QCL) (3), wherein the IR radiation is directed onto the sample (2) via a phase modulator (5) and at least one optical element (6), and detecting the IR radiation which is reflected and/or transmitted by the sample (2).

22 Claims, 13 Drawing Sheets

(51) Int. Cl.
*G01J 3/02* (2006.01)
*G01J 3/42* (2006.01)
*G02B 21/06* (2006.01)
*G02B 21/36* (2006.01)
*G01J 3/28* (2006.01)
*G01N 21/35* (2014.01)

(52) U.S. Cl.
CPC ............... *G01J 3/42* (2013.01); *G01N 21/35* (2013.01); *G02B 21/0096* (2013.01); *G02B 21/06* (2013.01); *G02B 21/361* (2013.01); *G01J 2003/423* (2013.01)

(58) Field of Classification Search
CPC . G01N 21/21; H04N 7/18; C12Q 1/68; C12Q 1/04; C12M 1/42
See application file for complete search history.

(56) References Cited

OTHER PUBLICATIONS

Kole, et al., "Discrete Frequency Infrared Microspectroscopy and Imaging with a Tunable Quantum Cascade Laser", Anal Chem 84, 10366-10372 (2012).

Lowenthal, et al., "Speckle Removal by a Slowly Moving Diffuser Associated with a Motionless Diffuser", Journal of Optical Society of America.

Patent Cooperation Treaty, International Searching Authority, Search Report and Written Opinion for PCT/EP2016/060230, 8 pages, dated Aug. 6, 2016.

Phillips, et al., "Hyperspectral microscopy of explosives particles using an external cavity quantum cascade laser", Optical Engineering 52(6), 061302-1-061302-8 (2013).

Yeh, et al., "Fast Infrared Chemical Imaging with a Quantum Cascade Laser", Anal Chem 87, 485-493 (2015).

* cited by examiner

MICROSCOPE FOR MOLECULAR SPECTROSCOPIC ANALYSIS

CROSS-REFERENCE TO RELATED APPLICATION(S)

This application claims priority to German Application No. 10 2015 107 148.7 filed on 7 May 2015.

FIELD OF THE INVENTION

The invention relates to a microscope for the molecular spectroscopic analysis of a sample, having a beam path having at least one quantum cascade laser (QCL) which emits an infrared (IR) radiation, a phase modulator which is arranged between the QCL and the sample, at least one optical element which is arranged between the phase modulator and the sample and a sensor which detects an IR radiation which is transmitted and/or reflected by the sample. The invention further relates to a method for the molecular spectroscopic analysis of a sample comprising the steps of irradiating the sample with an infrared (IR) radiation by means of a quantum cascade laser (QCL), wherein the IR radiation is directed onto the sample via a phase modulator and at least one optical element, and detecting the IR radiation which is reflected and/or transmitted by the sample.

BACKGROUND OF THE INVENTION

In order to treat diseases in an advantageous and successful manner, a reliable diagnosis is often essential. This is the case in particular for diseases which are not only treated in a purely symptomatic manner but in which a cause-specific treatment or healing is sought. A distinction between diseases simply on the basis of the symptoms thereof is often impossible because different diseases result in similar, partially overlapping symptoms although they can be attributed to different medical causes. Thus, changes of the tissue which are triggered by different organic malfunctions can lead to similar or even identical symptoms. For a successful, in particular cause-specific, treatment, account must be taken of these differences.

In order to comply with these medical requirements, the diagnosis works with biopsies, chemical/biological analyses or endoscopic examinations, by means of which the malfunction forming the basis of a disease is intended to be identified. In this case, biopsies are conventionally processed to form fine sections and the tissues or cells are dyed by suitable chemicals. However, the meaningfulness of fine sections dyed in this manner is substantially dependent on the interaction of the tissue with the dyes so that clear and reliable statements are often made more difficult by imperfect dyeing. Furthermore, this procedure is connected with a relatively large number of operating steps and is therefore relatively time-consuming. It can thereby also be used for operation-accompanying analysis only in a limited manner.

For these reasons, in recent years dye-free methods for examining tissues and cells have been developed. In this instance, there have become particularly established Fourier Transform Infrared (FTIR) analyses, in which biological samples are analysed on the basis of the natural IR transmission or reflection spectrum thereof. In this case, complete IR spectrums of the sample are recorded, either by means of point for point mapping (FTIR mapping) or by means of a parallel recording of a plurality of FTIR spectrums by means of an infrared detector with a focal plane arrangement (Focal Plane Array, FPA) (FTIR imaging). However, the conventional FTIR mapping is extremely time-consuming as a result of the point for point mapping. Although the method can be accelerated as a result of the parallel recording of a plurality of spectrums, the sensors (FPA) necessary for this purpose are extremely expensive.

Therefore, the use of one or more quantum cascade laser(s) (QCL) has been discussed in more recent times as an alternative to the established FTIR methods. This involves narrow-band infrared (IR) radiators which have a high spectral energy density and which generally radiate IR radiation of a defined narrow wavelength range. However, more modern devices can also be tuned by means of several hundred wavelengths and thus have a wider IR spectrum. However, reliable results could also previously be achieved with these devices only by using cost-intensive semiconductor detectors (for example, mercury/cadmium/tellurite (MCT) FPA) so that a substantial advantage over conventional FTIR technology has not been afforded in this regard.

Therefore, there is a need for cost-effective and rapid IR analysis devices and methods, in particular for examining biological samples.

STATEMENT OF INVENTION

In a first aspect, the invention relates to a microscope for the molecular spectroscopic analysis of a sample, having a beam path having at least one quantum cascade laser (QCL) which emits an infrared (IR) radiation, a phase modulator which is arranged between the QCL and the sample, at least one optical element which is arranged between the phase modulator and the sample and a sensor which detects an IR radiation which is transmitted and/or reflected by the sample, characterised in that the phase modulator is a rotatable IR-transparent scattering plate or a rotatable scattering mirror which reflects IR radiation, wherein the phase modulator rotates continuously during the analysis and is arranged in the beam path of the microscope in such a manner that no IR radiation which is scattered at the center of the phase modulator strikes the sample.

In a second aspect, the invention relates to a method for the molecular spectroscopic analysis of a sample comprising the steps of irradiating the sample with an infrared (IR) radiation by means of a quantum cascade laser (QCL), wherein the IR radiation is directed onto the sample via a phase modulator and at least one optical element, and detecting the IR radiation which is reflected and/or transmitted by the sample, characterised in that the phase modulator is a rotatable IR-transparent scattering plate or a rotatable scattering mirror which reflects IR radiation, wherein the phase modulator rotates continuously during the detection and no IR radiation which is scattered at the center of the phase modulator is directed onto the sample.

DESCRIPTION OF THE INVENTION

Figure 1:
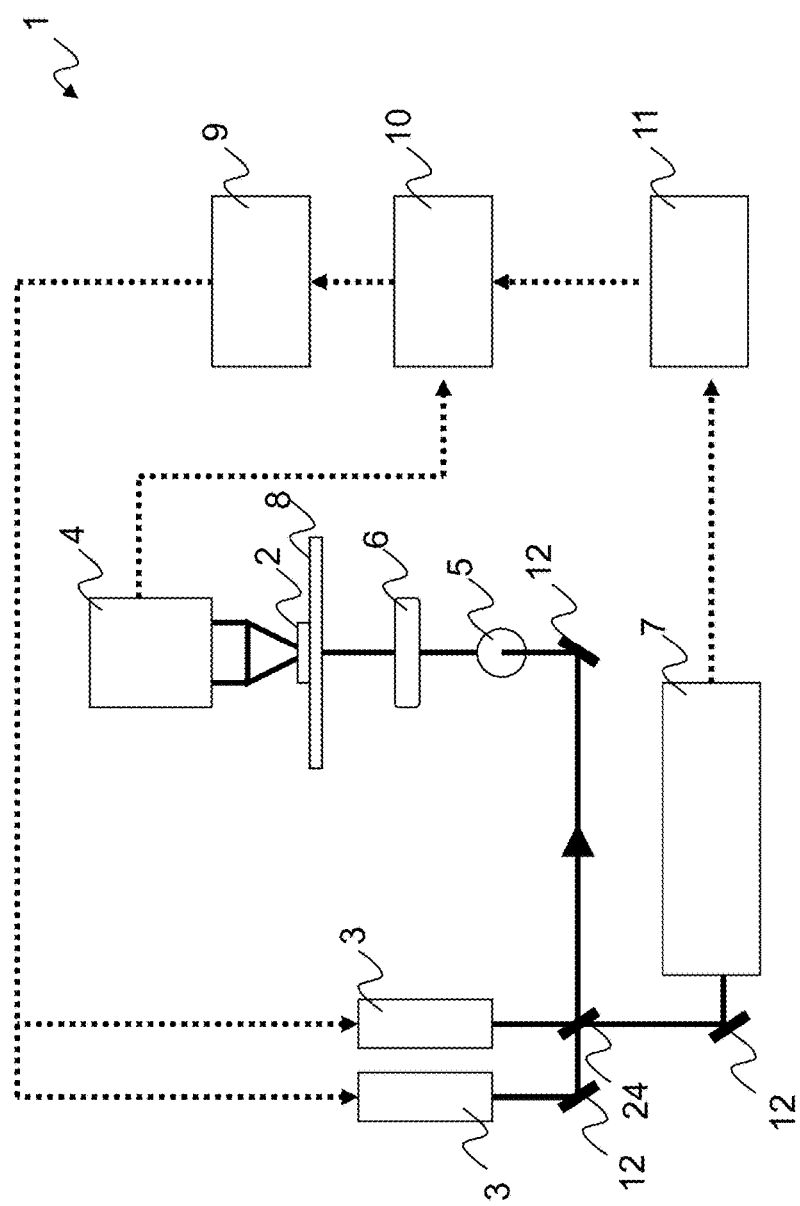
FIG. 1 is a schematic illustration of an IR microscope according to the invention.

In a first aspect, the invention relates to a microscope for the molecular spectroscopic analysis of a sample, having a beam path having at least one quantum cascade laser (QCL) which emits an infrared (IR) radiation, a phase modulator which is arranged between the QCL and the sample, at least one optical element which is arranged between the phase modulator and the sample and a sensor which detects an IR radiation which is transmitted and/or reflected by the sample. The phase modulator is a rotatable IR-transparent scattering plate or a rotatable scattering mirror which reflects IR radiation. By the phase modulator rotating continuously during the analysis and being arranged in the beam path of the microscope in such a manner that no IR radiation which is scattered at the center of the phase modulator strikes the sample, the spectral standard deviation of the absorbance spectrum of each pixel and therefore the measurement inaccuracy are significantly reduced. It is thereby possible to carry out molecular spectroscopic analyses using QCLs which have a similar accuracy to conventional Fourier Transform (FT) IR-based systems but which have significantly shorter measurement times.

Normally, an above-average large amount of interference, which occurs in particular at the optical elements of the beam path, is produced as a result of the high degree of coherence of the QCL. These occurrences of interference are usually eliminated mathematically by referencing with respect to a blank measurement. Since the interference pattern is dependent on wavelength, however, this referencing has to be carried out for each individual wavelength. This is possible either by a sample measurement and a reference measurement being carried out for each wavelength or by a reference measurement being recorded over the entire wavelength range. In order to carry out for each wavelength a sample measurement and a reference measurement, the sample would have to be removed from the beam path for each wavelength and inserted again. Not only is a high time consumption thereby produced, but also a substantial uncertainty in the positioning of the sample. However, a continuous referencing, in which initially the blank measurement is recorded for all the wavelengths and subsequently the measurement is again carried out for all the wavelengths, is not currently possible as a result of the technical circumstances of the QCL. The modification of the wavelength, at which a QCL emits, is generally carried out by a stepping motor tilting the tilting of a grid in an external cavity (Littrow configuration) quasi continuously over a selected angular range or in discrete steps. In this case, the positioning accuracy of the stepping motor necessarily results in errors in the angular position of the grid and consequently an incorrect adjustment of the wavelength of the laser. This results in variations of the interference pattern which do not allow elimination purely mathematically by the referencing with respect to a blank measurement.

As a result of the rotation of the phase modulator, however, there is produced a specific interference pattern or speckle pattern which is a function of the position of the phase modulator and which changes with the rotation thereof. However, it is constant for each individual rotation position. The spatial coherence of the IR radiation and the resultant interference effects are thereby significantly reduced over the averaged time so that a constant phase modulation and scattering are produced.

Since the phase modulator is a rotatable IR-transparent scattering plate or a rotatable scattering mirror which reflects IR radiation, the photons are distributed freely over the different directions in space. This is achieved in that scattering plates or scattering mirrors have a roughened surface on the side facing the QCL. A uniform phase shift does not take place so that the IR radiation which strikes the sample does not have any defined phase. Instead, the beams of the IR radiation strike the sample at differently modulated phases.

Furthermore, by the center of the phase modulator being exempted by the irradiation, the entire IR radiation which strikes the sample is detected by the modulation. If the center of the scattering plate which does not itself rotate (path speed=0) were to be included by the IR radiation and imaged on the sample, individual points of the sample would be irradiated by non-modulated IR radiation. At these points, the original interference caused by the QCL would disrupt the measurement. Instead, in the case of analyses with the microscope according to the invention, the 0 absorbance lines for each pixel are near the absolute 0 line without any substantial, potentially periodic fluctuations, as otherwise observed as a result of the coherence of a QCL (Yeh et al., 2015). In total, a mean value for the spectral standard deviation of less than 0.01 a.u. (absorbance units) could be achieved. This specific measurement accuracy allows the molecular spectroscopic analysis of complex samples with little absorbance and a fine structure, such as, for example, biological samples.

Furthermore, hyperspectral imagings of a sample with a spatial resolution of less than 20 µm are possible as a result of the high measurement accuracy. This cannot be achieved with conventional devices, as described, for example, in Phillips et al., 2013 because the remaining occurrences of interference and the resultant signal-to-noise ratio do not allow the registration of small absorbance jumps. However, a high spatial resolution is often indispensable for histopathological examinations. Furthermore, the produced hyperspectral imaging of the sample, even for extremely short measurement times of approximately 20 milliseconds, as used in spontaneous recordings with a fixed wavelength or with measurements with a high spectral resolution when the wavelength is tuned, is independent of the measurement time. It is thereby possible to observe changes of the infrared transparency of biological samples in real time with a spatial resolution capacity of less than 20 µm.

Figure 2:
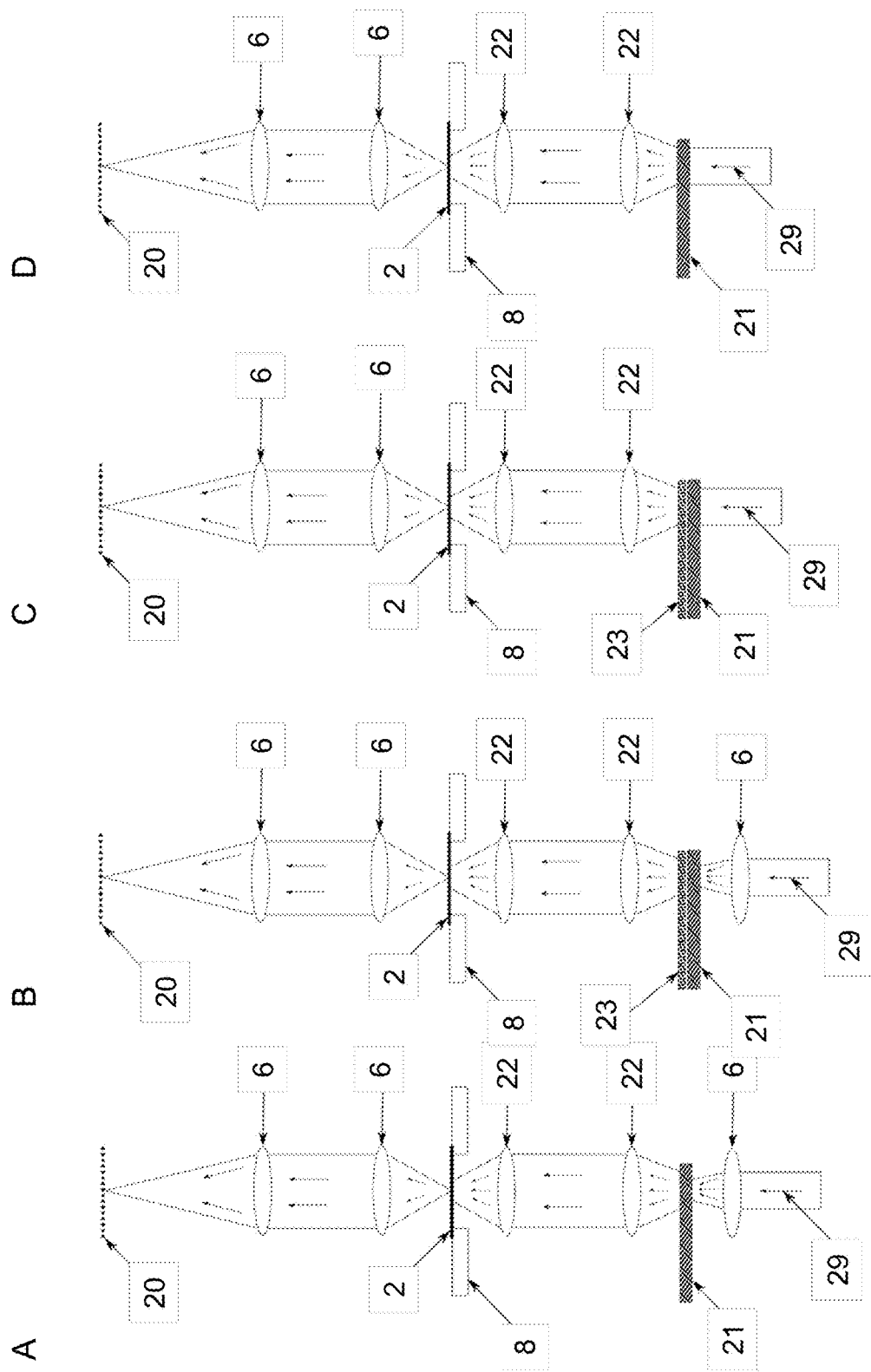
FIG. 2 shows various embodiments of the beam path of an IR microscope according to the invention by imaging the IR radiation onto the sample.
Figure 2:
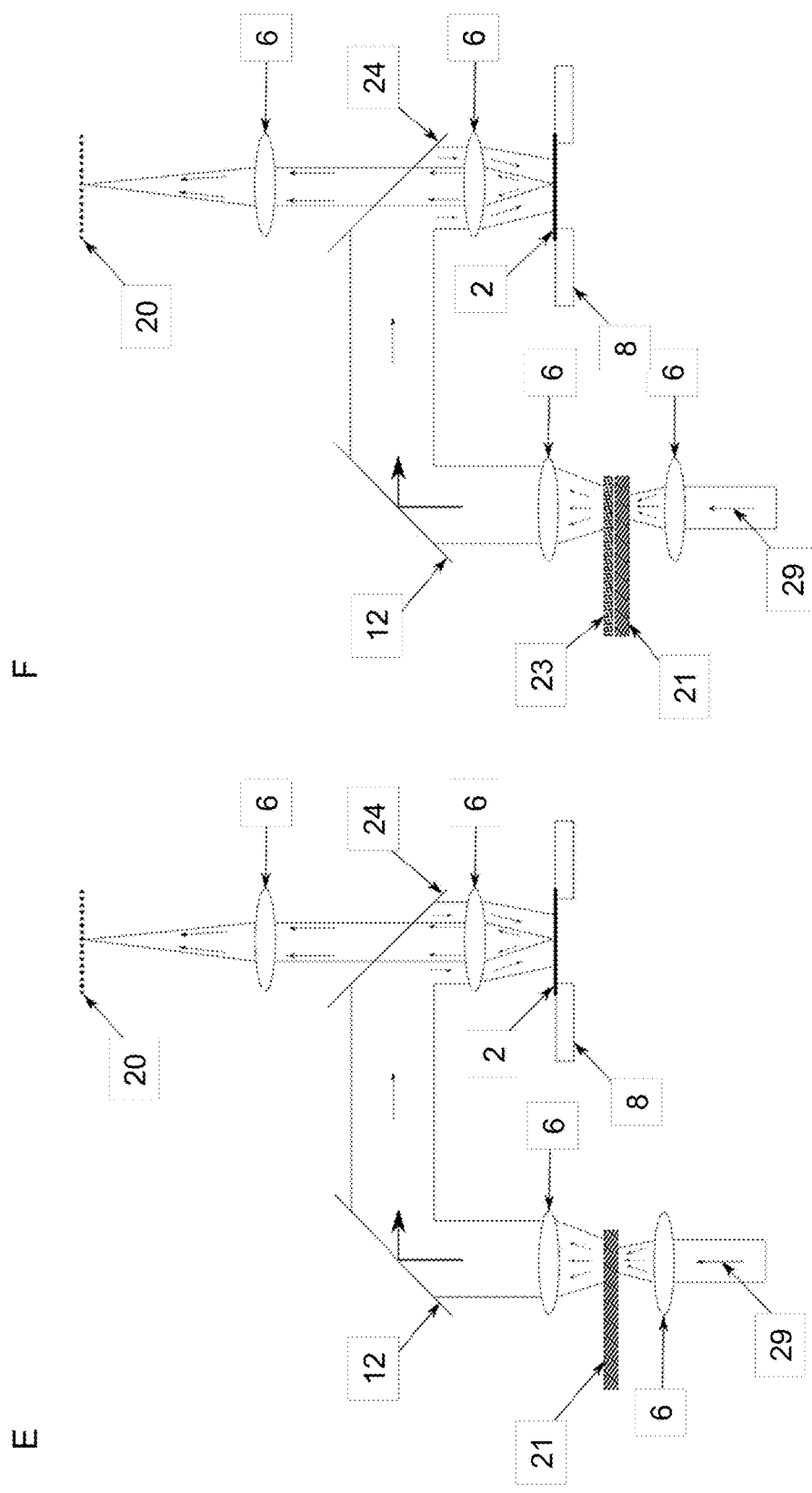
Figure 2:
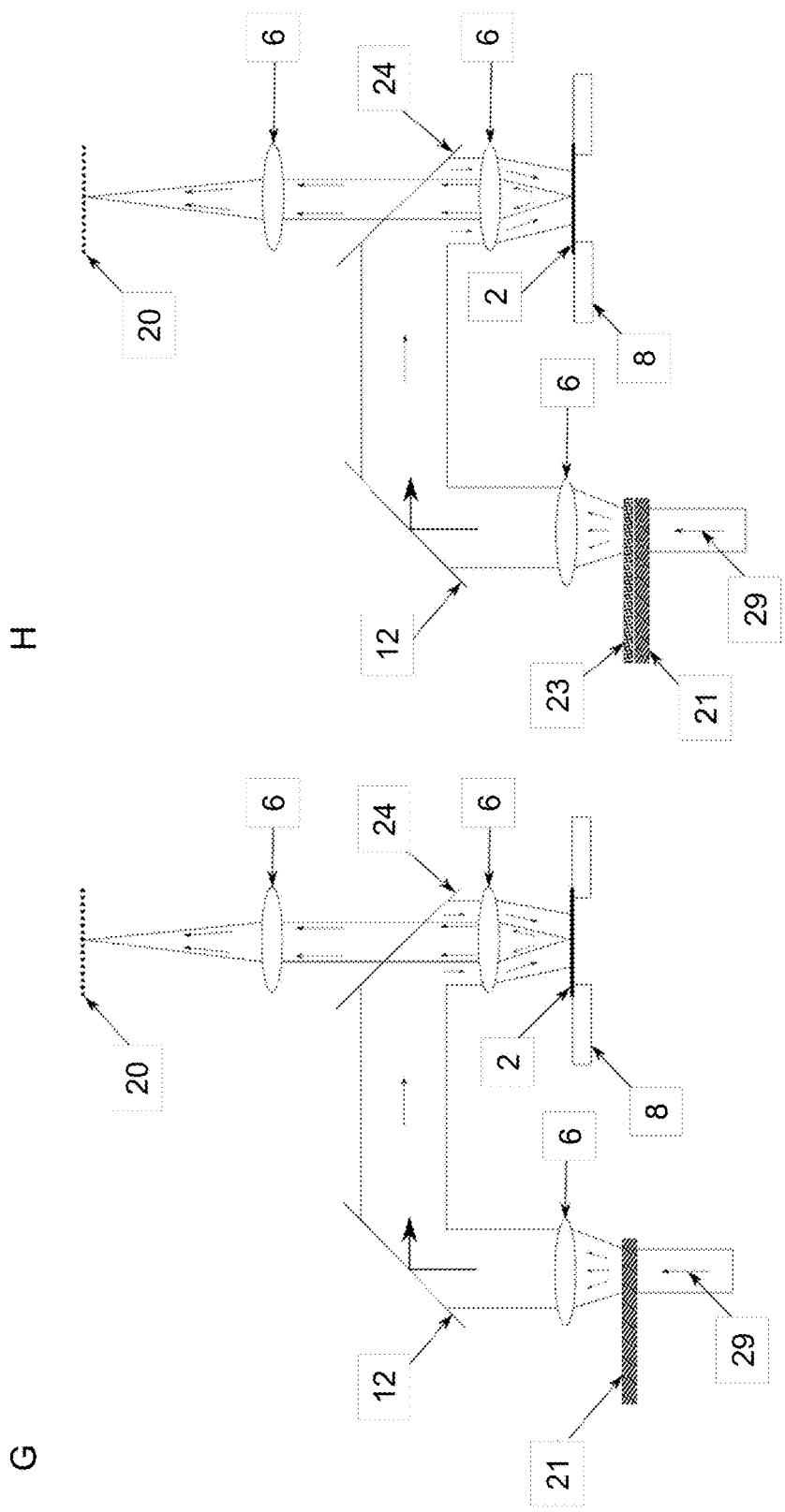
Figure 2:
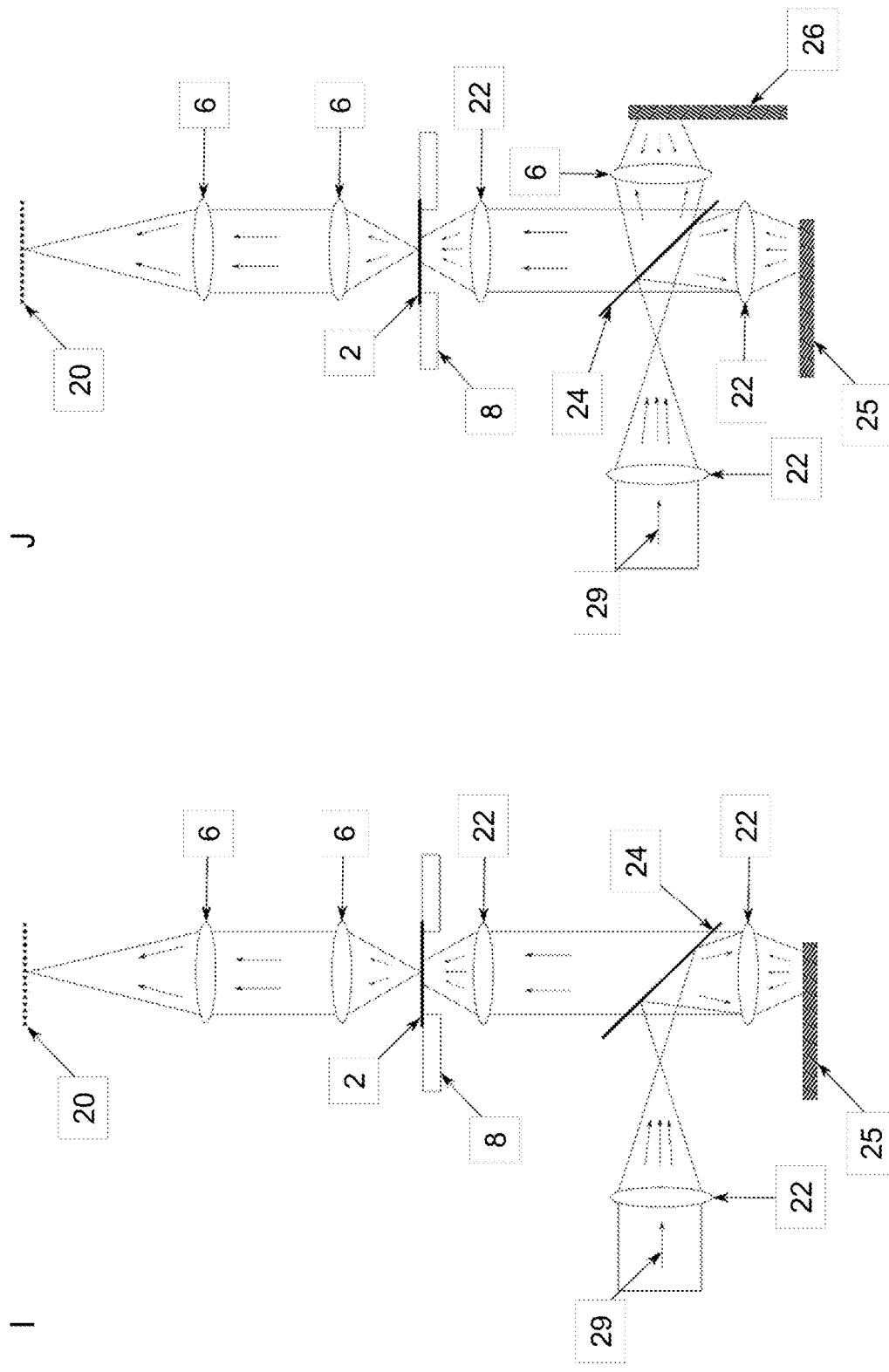
Figure 2:
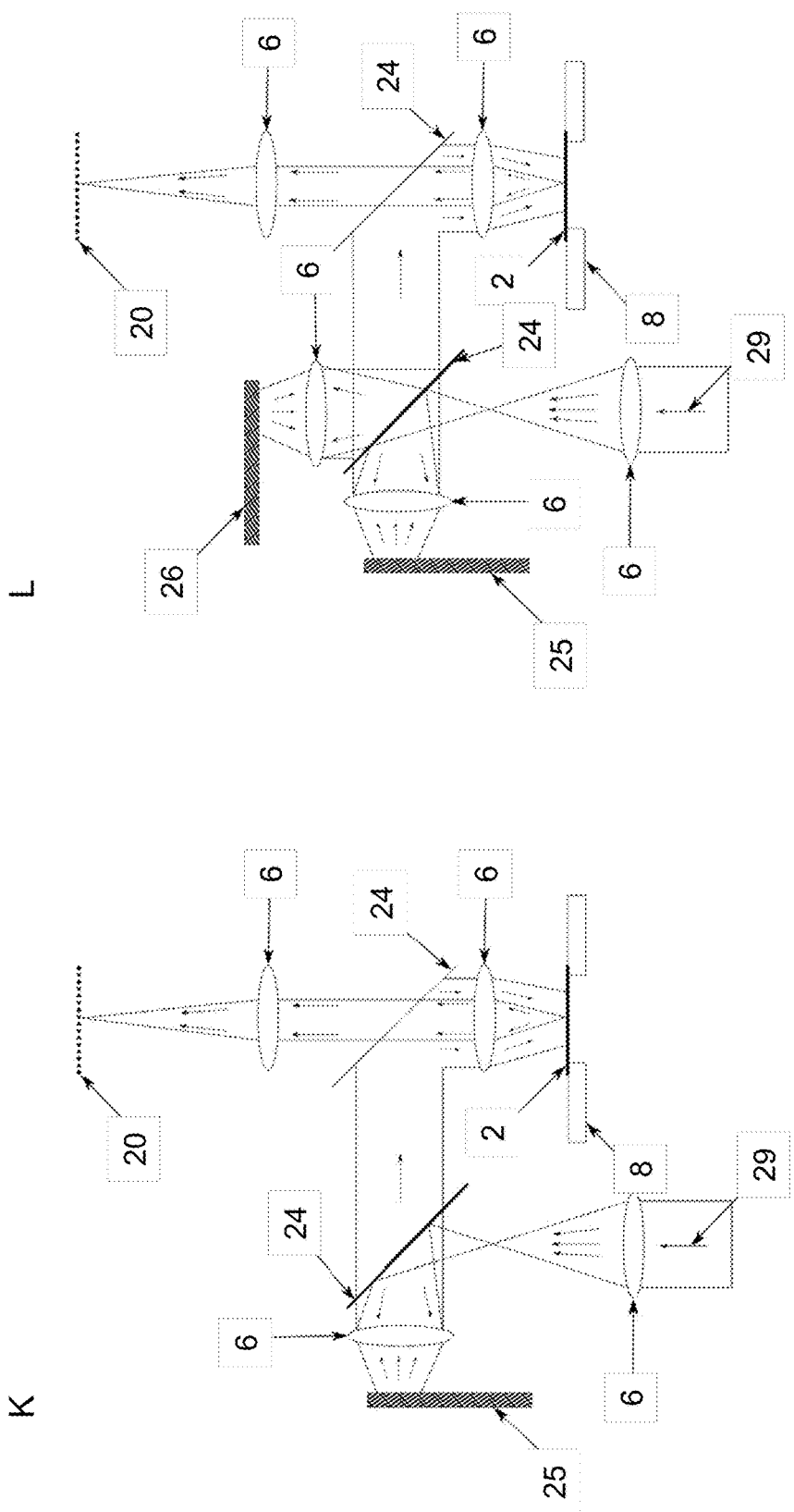

The QCL, the phase modulator, the at least one optical element and the sensor are arranged one behind the other in the beam path of the microscope, wherein the QCL and sensor form the start or end of the beam path (FIGS. 1, 3B). The at least one optical element is preferably used to expand the laser beam in order to illuminate the sample. Furthermore, additional microscopic elements, in particular optical elements, can be arranged in the beam path. For example, the phase modulator and the sample can be spatially separated from each other to such an extent that the rotating phase modulator can be decoupled from the remaining components of the microscope by a vibration-damping element. Furthermore, the illumination profile can be adapted to various microscopic requirements, for example, different magnification stages. Depending on the construction of the microscope, the analysis can further be carried out with transmission, reflection or transflection (FIG. 2). For a measurement with transflection, the sample is applied to an object carrier which reflects IR radiation so that the radiation passing through the sample is reflected by the object carrier and again passes through the sample before it is detected in accordance with a reflection measurement.

QCLs can emit the IR radiation either in a pulsed or in a continuous manner. For the microscope according to the invention both pulsed and continuous IR radiation can be used.

With the microscope according to the invention, a high number of pixels, for example, approximately 300,000 pixels, are measured in a parallel manner (imaging). A more rapid sample analysis than in a point for point mapping is thereby possible. Sensors which are suitable for the microscope according to the invention, such as, for example, microbolometers, currently allow the parallel measurement of from approximately 1000 to approximately 1,300,000 pixels, wherein greater formats are being developed.

In a preferred embodiment, the microscope is a wide-field microscope. In wide-field microscopy, the image sections are relatively large and contain a lot of interference. As a result of the use of a rotating phase modulator, these occurrences of interference can be minimised and eliminated mathematically.

In a preferred embodiment, the sample is a non-dyed sample, preferably a non-dyed tissue sample. The microscope according to the invention is particularly suitable for examining a sample on the basis of the inherent biochemical properties thereof, that is to say, on the basis of the IR transmission or reflection thereof. The IR transmission or reflection of the sample is directly dependent on the biochemical composition thereof so that a dyeing of the sample, for example, by cell dyes or antibodies, is unnecessary. Significant operating steps and consequently time can thereby be saved. This is particularly important in the case of analyses accompanying operations because the operation should not be extended where possible by external operating steps.

In order to achieve the situation that no IR radiation which is scattered at the center of the phase modulator strikes the sample, the microscope or the beam path thereof can be adapted in different manners. In a preferred embodiment, the phase modulator is arranged in the beam path of the microscope in such a manner that the center of the phase modulator is not included by the IR radiation. No IR radiation which is scattered at the center of the phase modulator is thereby produced.

In another embodiment, the beam path has a cover which is arranged behind the center of the phase modulator and in front of the sample, wherein the cover blocks the IR radiation which is scattered at the center of the phase modulator.

In another embodiment, the beam path has a lens arrangement which is arranged between the phase modulator and the sample, wherein the lens arrangement directs only the IR radiation which is scattered outside the center of the phase modulator onto the sample.

In a preferred embodiment, no IR radiation which is scattered in the inner third of the surface of the phase modulator strikes the sample. To this end, only a region outside the inner third of the surface of the phase modulator is preferably included by the IR radiation. At the center of the phase modulator, the path speed is equal to 0 so that at the center of rotation (center) of the phase modulator no phase modulation takes place. The path speed continuously increases outwards. Accordingly, near the center only a slow phase modulation is produced; in the edge region of the phase modulator where the path speed is highest, however, a correspondingly more rapid phase modulation is produced. In a particularly preferred embodiment, only an IR radiation which is scattered in the outer third of the surface of the phase modulator strikes the sample. To this end, only a region outside the inner two-thirds of the surface of the phase modulator is preferably included by the IR radiation.

In a preferred embodiment, no IR radiation which is scattered in a region of at least 1 mm, preferably at least 2 mm, more preferably at least 5 mm, more preferably at least 10 mm, more preferably at least 20 mm around the center of the phase modulator strikes the sample. This is preferably achieved in that only a region outside at least 1 mm, preferably at least 2 mm, more preferably at least 5 mm, more preferably at least 10 mm, more preferably at least 20 mm around the center of the phase modulator is included by the IR radiation. When the phase modulator is illuminated with a Gaussian infrared beam, it is preferable for the beam center of the infrared beam to strike the phase modulator in a region outside at least 1 mm, preferably at least 2 mm, more preferably at least 5 mm, more preferably at least 10 mm, more preferably at least 20 mm around the center of the phase modulator. Near the center of the phase modulator, only a slow phase modulation is produced. The path speed increases with greater distance from the center of the phase modulator and a correspondingly more rapid phase modulation is produced.

In a preferred embodiment, the QCL emits the IR radiation in the form of a laser beam, the diameter of which at the point of impact on the phase modulator is smaller than the radius of the phase modulator. It is thereby possible to direct the laser beam selectively onto a region at the other side of the center of the phase modulator and nevertheless to image it completely by means of the phase modulator on the sample. To this end, for example, there can be used a phase modulator which has a correspondingly greater diameter than the laser beam. Alternatively, the QCL beam can be focused by optical elements on the phase modulator so that it has a correspondingly small diameter at the location of the phase modulator.

In a particularly preferred embodiment, the diameter of the laser beam is at the point of impact on the phase modulator 80% or less, preferably 70% or less of the radius of the phase modulator. The beam can thereby be directed precisely onto a region outside the inner third of the surface of the phase modulator. If the radius of the phase modulator is, for example, 25.4 mm, a QCL beam having a diameter less than 10 mm can be directed onto the edge region of the phase modulator without illuminating the center thereof.

In a preferred embodiment, the microscope has at least two, preferably three, more preferably four, QCLs. QCLs are semiconductor lasers which produce middle or far infrared radiation. The radiation can be fixed either at a defined frequency range of generally from 1 to 2 $cm^{-1}$ or changed by tuning. In particular QCLs in an external cavity are suitable for tuning (external cavity quantum cascade laser/EC-QCL) and generally cover a spectral range with a width of several 100 cm$^{-1}$. With these QCLs, greater portions of the IR spectrum can be recorded. Depending on the type of the molecular spectroscopic analysis, one or more QCLs can be used. Under some circumstances, the recording of a small number, for example, only two, different wavelengths may already be sufficient for the analysis of biological samples. Depending on the bandwidth, one or two QCLs can be used therefor, whereby a relatively rapid measurement can be carried out. However, should a broader spectral range be covered, one or more tunable QCLs can be used sequentially.

In a preferred embodiment, the QCL is a QCL in an external cavity (EC-QCL). These QCLs are distinguished by a high brilliance and a high spectral energy density. Furthermore, they can be tuned over a relatively wide wavelength range. EC-QCL are consequently particularly preferable for recording wider IR spectrums and allow a rapid, relatively high-resolution IR measurement.

In a preferred embodiment, the QCL is continuously tuned during the analysis. The use according to the invention of a phase modulator allows the reference measurement and the measurement of the sample to be included separately for the entire wavelength range to be recorded. Consequently, it is possible to record a continuous section of the IR spectrum, on the one hand, for the reference and, on the other hand, the sample. This is particularly advantageous if larger regions of the spectrum are intended to be recorded in order to obtain detailed information about the chemical and biological composition of the tissue.

In a preferred embodiment, the QCL is tuned during the analysis at a speed of from 5 cm$^{-1}$/s to 30 cm$^{-}$/s, preferably at a speed of from 10 cm$^{-1}$/s to 20 cm$^{-1}$/s, more preferably at a speed of approximately 10 cm$^{-1}$/s. The tuning should be carried out as rapidly as necessary and as slowly as possible in order to obtain an interference-free result. In this case, the minimum speed is orientated towards the desired spectral resolution. If, for example, it is desirable to have a resolution of four wave numbers, every two wave numbers it is necessary to have an independent measurement point. At a tuning speed of 10 wave numbers per second, this means that every 0.2 seconds an independent measurement point is included. In accordance with the speed of the sensor, this may already be sufficient for a spectroscopic reproduction of the sample. For example, a microbolometer camera with a frame rate of 50 Hz can record 10 images in 0.2 seconds. The result can subsequently be averaged over these images. In the case of cameras with a frame rate of only 5 Hz, however, in 0.2 seconds only a single image could be recorded so that here a smaller tuning speed is recommended. Conversely, the frame rates of MCF-FPA detectors are in the range of kilohertz so that in this case the rotation speed of the phase modulator determines the maximum tuning speed. In order to obtain an illumination profile which is independent over the averaged time, for each measurement at least one rotation of the phase modulator must be carried out. In the case of a rotation rate of, for example, 1000 Hz, therefore, each millisecond a new independent measurement point can theoretically be included, provided that the frame rate of the detector allows this. If an independent measurement point is intended to be generated every two wave numbers, the laser can be tuned with two wave numbers per millisecond or 2000 wave numbers per second.

In a preferred embodiment, the IR radiation emitted by the QCL is in a range from 5 to 12.5 μm. This corresponds to a wave number of from 800 to 2000 cm$^{-1}$ and covers the spectral range of the IR radiation in which the majority of biological information is contained. In addition, lipids in the wavelength range from approximately 2.7 to 3.7 μm can be detected (corresponds to approximately 3000 wave numbers). The measurement can be carried out, for example, on the basis of individual fixed laser modules, wherein the measurement of two independent wavelengths for a detailed reproduction of a tissue sample may already be sufficient. Such measurements can be carried out depending on the wavelength with one or two conventional QCLs and are consequently particularly cost-effective. Measurements can also be carried out with tunable lasers at individual selected wavelengths, wherein the number of images to be recorded is greatly reduced in relation to a wider spectrum and the analysis is accordingly accelerated.

In a preferred embodiment, the sensor is a thermal sensor, preferably a microbolometer. By using a phase modulator according to the invention in a microscope, it is possible to use a QCL independently of the detection speed and sensitivity of the sensor used. In order to reduce the measurement inaccuracies which are produced as a result of the coherence of the QCLs, work was previously carried out with highly sensitive and rapid MCF-FPAs which are nitrogen-cooled. However, they are very expensive. Furthermore, the systematic measurement errors when using a QCL also cannot be completely corrected by MCF-FPAs so that the 0 absorbance lines of individual pixels fluctuate powerfully about the absolute 0 line (Yeh et al., 2015). Using a rotating phase modulator, wherein the center of the phase modulator is exempted by the illumination by the QCL, however, highly specific measurements can be carried out even with relatively slow thermal detectors (for example, at time constants of over 5 microseconds).

In particular pyroelectric detectors and microbolometers may be considered as thermal sensors which cannot be used for conventional FT-IR measurements as a result of the slow speed thereof. In particular, the use of non-cooled microbolometers is possible, wherein microbolometers in the form of a so-called "focal plane array" (FPA) are preferable. Microbolometer FPA detectors are relatively cost-effective both to obtain and during operation because they do not require any energy-intensive cooling or any vacuum pump for maintenance. However, they do have some disadvantages which previously prevented the use thereof for molecular spectroscopic analyses, in particular using QCLs. Microbolometer FPA detectors measure the incident IR radiation via a heating of the pixels which accompanies a change of the electrical resistance. In comparison with MCT-FPA detectors, they are relatively slow with time constants in the range from 7 to 10 milliseconds. Therefore, even rapid microbolometer FPA are generally limited to 50 Hz currently. Furthermore, the pixels cannot be directly released in commercial microbolometers, for which reason image recordings are recorded with a delay in the case of microbolometer FPA detectors with a frame rate of 50 Hz where applicable by from 2 to 5 milliseconds relative to the "desired acquisition time". However, this minimal delay is sufficient in order to change the sequence of the interference images during the phase-continuous tuning of a QCL so that a conventional mathematical correction of the interferences by referencing with respect to a single blank measurement would be erroneous. This is not the case with the use of a phase modulator according to the invention. Furthermore, the microscope structure according to the invention allows the relatively large surface of a microbolometer FPA to be completely used. To this end, it is necessary to illuminate in a completely homogeneous manner the surface of the microbolometer FPA which may be more than 100 mm$^2$. This is not possible without a phase modulator as a result of the powerful occurrences of interference which occur during the use of QCL. Furthermore, the measurement time which is reduced as a result of using the QCL and the phase modulation contributes substantially to the successful use of microbolometer FPA detectors. In that the detectors are non-cooled, their waste heat can be reflected in the sample which is intended to be examined and can be perceived by the sensor as a signal (so-called Narcissus effect). However, fluctuations of the temperature of the sensor during the recording can be eliminated mathematically only to a limited extent so that errors increase with the length of the measurement time.

In a preferred embodiment, the microbolometer has a frame rate of from 30 to 60 Hz, preferably from 40 to 60 Hz, more preferably of approximately 50 Hz. The thermal time constant of conventional bolometer pixel elements is approximately from 7 to 10 milliseconds. As a result, frame rates of approximately from 30 to 50 Hz are possible. They are readily suitable for ensuring a precisely detailed and reliable reproduction of the sample.

In a preferred embodiment, the surface normal of the phase modulator is parallel with the rotation axis. A beam offset which is dependent on the rotation phase is thereby prevented from being produced and influencing the reference measurement and sample measurement differently, and leading to measurement inaccuracies.

This is particularly advantageous in the case of relatively slow rotation speeds of the phase modulator.

The phase modulator is a rotatable IR-transparent scattering plate or a rotatable scattering mirror which reflects IR radiation. Depending on whether a scattering plate or a scattering mirror is used for the microscope construction according to the invention, the beam path of the microscope differs. Thus, the IR radiation of the QCL falls through the scattering plate and the at least one optical element falls on the sample, whereas a scattering mirror reflects the radiation of the QCL and it is then directed via at least one optical element onto the sample. IR-transparent scattering plates preferably comprise silicon, germanium, KRS6 thallium bromo-chloride, amorphous material transmitting infrared radiation (AMTIR), barium fluoride, calcium fluoride, silver halide (silver bromide, silver chloride), zinc selenide, zinc sulphide, diamond or potassium bromide. A fine homogeneous structure can be formed at the surface of these materials, for example, by photolithography or isotropic wet etching, so that the scattering on the phase modulator in each pixel of the image field is the same over a fixed time on average. The variance between the measurements is thereby reduced. Scattering mirrors which reflect IR radiation which may be considered include both gold mirrors which are preferred in particular for the middle infrared radiation and silver mirrors. Furthermore, materials with a particularly high refraction index, such as, for example, silicon or germanium, can also be used.

In a preferred embodiment, the width of the angular distribution of the IR radiation which is transmitted by the scattering plate or reflected on the scattering mirror is at least 1°, preferably at least 2°, more preferably at least 5°, more preferably at least 8°, more preferably at least 10°, more preferably at least 12°, more preferably at least 15°.

Figure 8:
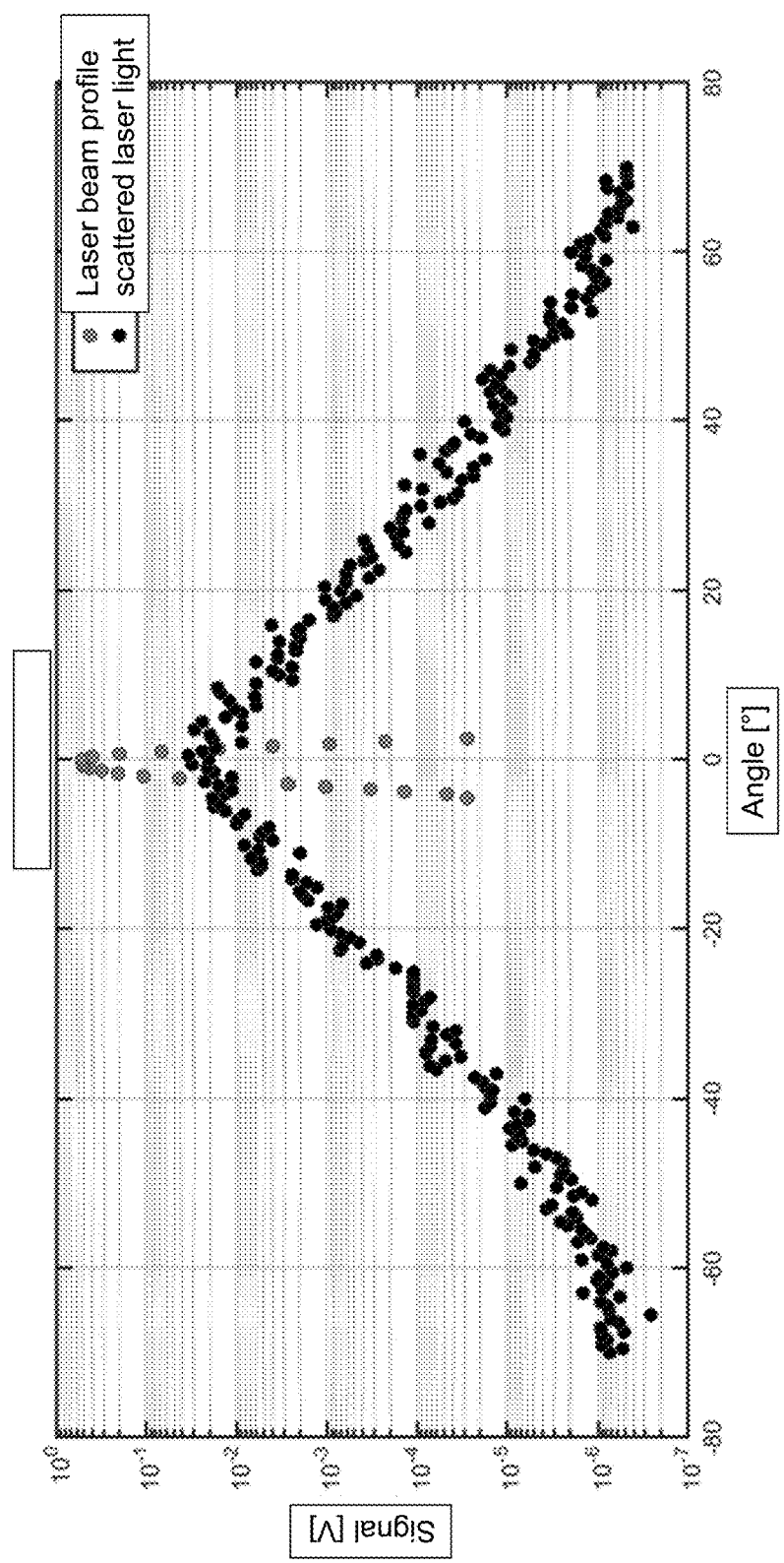
FIG. 8 shows the non-scattered laser beam profile of the QCL and the laser beam profile after the scattering by the scattering plate or the scattering mirror.

The angular distribution describes the distribution of the radiation over the different directions in space. The angular distribution of the IR radiation is changed by the scattering plate or the scattering mirror (FIG. 8). Before the IR radiation of the QCL strikes the scattering plate or the scattering mirror, it has a narrow angular distribution (laser beam profile in FIG. 8). As a result of the scattering plate or the scattering mirror, there takes place a scattering by which the angular distribution of the IR radiation is expanded (scattered laser light in FIG. 8). As a result of the great width of the angular distribution of the IR radiation which is transmitted by the scattering plate or reflected on the scattering mirror, a chaotic phase modulation is achieved.

In a preferred embodiment, the scattering plate is a roughened silicon plate.

In a preferred embodiment, the phase modulator has at the side facing the QCL a structured surface. As a result of the structuring of the surface which is orientated towards the QCL, it is ensured that the laser beam is not reflected directly and thus could damage the laser source. A structured surface can be produced, for example, by sand-blasting or chemical etching. Such a processing operation is generally sufficient to ensure the protection of the laser source, particularly if the distance between the laser beam outlet and the scattering plate is at least 1 m.

In a preferred embodiment, the phase modulator is positioned at an angle of at least 0.5° relative to the radiation of the QCL. In order to prevent reflection of the QCL on the radiation source, the phase modulator can be moved into a position which is oblique in relation to the laser beam. The oblique arrangement can be used in place of or in conjunction with the structuring of the surface of the phase modulator. Alternatively, however, a Faraday isolator can also be used in order to protect the radiation source.

In a preferred embodiment, the phase modulator rotates at a rate which is at least 5%, preferably at least 8% higher than a frame rate of the sensor. The inventors have established that the spectral standard deviation of the absorbance spectrum of each pixel can be further reduced and therefore the measurement accuracy can be further increased by the phase modulator continuously rotating at a rate which is at least 5% higher than the frame rate of the sensor. As a result of the higher rotation rate of the phase modulator in comparison with the frame rate of the sensor, the reduction of the spatial coherence of the IR radiation over the averaged time is reached particularly quickly at the same time. Generally, a high level of measurement accuracy thereby becomes possible with short measurement times. This is particularly decisive for analyses of biological samples accompanying operations.

For example, a sensor having a frame rate of 50 Hz records 10 images in 0.2 seconds. The result can subsequently be averaged over these images. At a frame rate of the sensor of 50 Hz, the rotation rate of the phase modulator is at least 52.5 Hz. In the case of a sensor having a frame rate of 5 Hz, in 0.2 seconds only a single image is recorded. In this case, the rate at which the phase modulator rotates is at least 5.25 Hz.

In a particularly preferred embodiment, the phase modulator rotates at a rate which is at least 15%, preferably at least 20% higher than the frame rate of the sensor. The measurement inaccuracy is thereby even further reduced. For example, the inventors have obtained a substantial reduction of the spectral standard deviation of the absorbance spectrum of each pixel for a frame rate of the sensor of 50 Hz and a rotation rate of the phase modulator of 60 Hz. A rotation rate of the phase modulator of 62.5 Hz for a frame rate of the sensor of 50 Hz also provided very precise measurement results.

In a preferred embodiment, the phase modulator rotates at a rate of at least 10 Hz, preferably at least 20 Hz, more preferably at least 30 Hz, more preferably at least 50 Hz, more preferably at from 50 to 200 Hz. In order to obtain a minimum measurement time, the phase modulation and scattering should be as constant as possible over a measuring point. A plurality of measurements are thereby prevented from having to be carried out and integrated for each wavelength, whereby the measurement time would generally be substantially increased. In order to obtain a sufficiently constant phase modulation over the measuring point, at least one complete rotation of the phase modulator during a measuring point is necessary. The construction of the microscope allows, for example, the use of phase modulators with diameters of up to two inches and rotation speeds of up to 200 Hz. Depending on the size of the phase modulator, it is also possible to obtain sufficiently high path speeds in the edge region of the phase modulator with lower rotation rates in order to minimise the spatial coherence over the averaged time. For the production of a particularly homogeneous and interference-free hyperspectral image, path speeds of from 5 to 35 m/s have been found to be particularly advantageous. Rotation rates between 50 and 100 Hz were sufficient to measure at tuning speeds of up to 30 $cm^{-1}$ per second and at a spectral resolution of 2 $cm^{-1}$ (approximately 30 milliseconds per independent measuring point). In a particularly preferred embodiment, therefore, the phase modulator rotates at a rate of from 50 to 100 Hz. If the QCL is tuned, for example, at 10 $cm^{-1}$ per second and if an independent measuring point is intended to be available every 1 $cm^{-1}$, the phase modulation and scattering must be comparable on average over time ranges of 0.1 seconds. For a rotation rate of 50 Hz, this corresponds to five rotations of the phase modulator, whereby precise measurements are possible.

In another embodiment, the phase modulator rotates at a rate of at least 52.5 Hz, preferably at least 54 Hz, more preferably at least 60 Hz, more preferably from 60 to 200 Hz, more preferably from 80 to 180 Hz, more preferably from 100 to 150 Hz.

In a particularly preferred embodiment, the rotation rate of the phase modulator is not a whole-number or half-integer multiple of the frame rate of the sensor. That is to say that the phase modulator rotates at a rotation rate (n) of n=x*m, where m is the frame rate of the sensor and x is a (positive) real number with the exception of all the natural numbers. Particularly in the case of relatively long measurement times, a phase shift is produced between the phase modulator and the image recording by the sensor. This risk particularly exists when a thermal sensor with a particularly slow frame rate does not function constantly. The phase shift then results in measurement inaccuracies which can influence the result negatively. In this case, the rotation rate of the phase modulator should be a whole-number or a half-integer multiple of the frame rate of the detector. If the detector functions at a very constant and rapid frame rate (for example, an MCT-FPA), however, no corresponding restriction of the rotation of the phase modulator is necessary. Furthermore, with relatively slow detectors (for example, microbolometers), the problems of a phase shift can also be avoided by the length of the individual measurement time periods being shortened, preferably to less than 0.5 seconds. This can be achieved inter alia by only individual wavelengths being detected instead of recording a complete spectrum. For example, only 0.38 seconds are necessary to record 19 images at a single wavelength and with one detector at a frame rate of 50 Hz. With such short measurement time periods, a rotation of the phase modulator in phase with the detection is not only possible, but even advantageous because the highest level of measurement precision which is intended to be obtained can thus be achieved.

In a preferred embodiment, the at least one optical element is constructed in such a manner that both the sample and the detector are illuminated completely and homogeneously. In this case, the at least one optical element is preferably positioned between the phase modulator and sample in such a manner that the acceptance angle of the objective lens is completely illuminated for the detection of the IR radiation which is emitted by the sample.

In a preferred embodiment, the at least one optical element is constructed in such a manner that the IR radiation is imaged on the aperture diaphragm which is located in the focal plane of a capacitor. This configuration which corresponds to a Köhler illumination produces an extraordinarily homogeneous and interference-free hyperspectral image and therefore allows a particularly exact reproduction of the sample.

In an alternative embodiment, the at least one optical element is constructed in such a manner that the region of the phase modulator illuminated by the IR radiation is imaged on the sample. If the region of the phase modulator illuminated by the IR radiation is imaged directly on the sample, an imaging at the ratio of from 0.7 to 1.3, preferably from 0.8 to 1.2, more preferably of approximately 1 is advantageous. By the radiation spot being imaged onto the sample at approximately 1:1 by radiation coming from the phase modulator, it is illuminated completely and homogeneously, whereby the formation of interferences and therefore measurement inaccuracies is reduced.

In a preferred embodiment, the microscope has at least one additional optical element which is arranged between the QCL and the phase modulator. The additional optical element can bring about, for example, a parallelisation of the expanded laser beam.

In order to regulate the magnitude of the illumination spot on the phase modulator, an optical element which can be adjusted in terms of the position thereof can be arranged between the QCL and the phase modulator. As a result of the shift of the position of the optical element relative to the phase modulator, the magnitude of the illumination spot on the phase modulator can be adjusted, wherein the additional optical element is preferably positioned so that the acceptance angle of the objective lens which is used for detection is completely illuminated.

In a preferred embodiment, each optical element is a lens or an objective lens independently of each other.

In a preferred embodiment, each lens comprises, independently of each other, a material which is selected from the group comprising zinc selenide, zinc sulphide, silicon, germanium, sodium chloride, barium chloride, calcium fluoride, potassium bromide, silver halides (silver bromide/silver chloride), KRS6 thallium bromo-chloride, amorphous material transmitting infrared radiation (AMTIR) and diamond. Depending on the wavelength of the IR radiation of the QCL, the use of different materials may be advantageous. For example, zinc selenide lenses are particularly suitable for recording particularly wide spectrums. The microscope may also have a plurality of different lenses. Thus, a plurality of individual lenses (see, for example, FIG. 2) or a mirror objective lens can be used for imaging the radiation spot of the phase modulator on the sample.

In a preferred embodiment, the microscope has a second static phase modulator. This second phase modulator is preferably arranged in the beam path downstream of the rotating phase modulator, that is to say that the light of the QCL first falls on the rotating phase modulator and subsequently on the static phase modulator. The static phase modulator differs from the first phase modulator in that it does not rotate. By using the second phase modulator, the rotation artefacts ("swirling patterns") which are produced by the rotating phase modulator are substantially reduced, whereby the spatial coherence of the QCL laser radiation further decreases over the averaged time. Therefore, when an additional static phase modulator is used, lower rotation rates of the rotating phase modulator are sufficient in order to generally reduce the interferences substantially. If the QCL is tuned, for example, at only approximately 2 cm$^{-1}$ per second every 1 cm$^{-1}$, that is to say, every half second, an independent measuring point has to be recorded for a desired spectral resolution of 2 cm$^{-1}$. By using two phase modulators, the phase modulation and scattering are also comparable in the case of slow rotation rates of the rotating scattering plate over the averaged time over 0.5 seconds so that rotation frequencies of 2 Hz, that is to say, a complete rotation of the phase modulator per measuring point, are already sufficient in order to carry out reliable measurements. This not only reduces the wear of the bearing of the rotating phase modulator, but also allows the use of ball-supported phase modulators which are substantially more cost-effective.

In a preferred embodiment, the microscope has a device for referencing. A referencing allows the control of the laser power and the wavelength during the measurement. It may, for example, be carried out by means of a phase-dependent interferometer or by a thermally stabilised gas cell which is filled with a gas which absorbs in the spectral measurement range (for example, ethanol).

In a preferred embodiment, the phase modulator is mounted on a precisely supported rotation shaft. An exact positioning of the phase modulator is thereby achieved and allows a reproducible production of successive interference patterns. For example, plain bearings, roller bearings, ball bearings, angular ball bearings, four-point bearings, toroidal roller bearings, spherical roller bearings, needle bearings, cylindrical roller bearings, self-aligning ball bearings, self-aligning roller bearings, ball roller bearings, tapered roller bearings, deep groove ball bearings, hybrid bearings, Cronidur roller bearings, air bearings, hydrostatic plain bearings, hydrodynamic plain bearings or magnetic bearings are suitable for the precise bearing of the rotation shaft. These bearings can withstand a high rotation rate of the phase modulator. When there are used bearings which are unsuitable for high rotation rates of the phase modulator, however, damage to the bearings already occurs after a short time.

Spindle bearings are preferred from among the angular ball bearings.

Preferred deep groove ball bearings are hybrid bearings with roller members comprising silicon nitride (ceramic material) and bearing rings comprising steel. Such bearings are also referred to as hybrid ceramic bearings.

Combinations of a plurality of bearings are preferred, such as, for example, fixed/movable bearings, in which the fixed bearing axially guides the shaft and fixed and movable bearings radially support the shaft.

In a preferred embodiment, the rotation shaft is supported by high-speed bearings. High-speed bearings are advantageous at a high rotation rate of the phase modulator and in particular in the case of long measurement time periods because they allow a constant rotation rate over long times. When other bearings are used, there is the risk that the rotation rate of the phase modulator may not be sufficiently constant over a longer time because drops in the speed often occur as a result of the heating of the bearings over time. Therefore, they are not suitable for long measurements. High-speed bearings further have a service-life of several years so that the inventors have previously not observed any failure of such bearings. As a result of the high service-life of the high-speed bearings, the maintenance complexity of the microscope is reduced.

In a preferred embodiment, the rotation shaft is supported by a fixed/movable bearing with high-speed bearings. The bearings are thereby not damaged during heating of the rotation shaft. This is particularly advantageous in the case of high rotation rates of the phase modulator. Alternatively, however, arrangements with mutually adjacent bearings and floating bearings can also be used for the bearings of the rotation shaft and successful measurements could also be carried out therewith.

When non-sealed bearings are used, the service-life of the bearings during high-speed operation is limited to a few days. Therefore, the bearings are pre-lubricated bearings which are sealed at both sides in a preferred embodiment.

Hybrid ceramic bearings, in particular sealed hybrid ceramic bearings, are particularly preferred because they have a long service-life at high rotation rates of the phase modulator. The maintenance complexity of the microscope is thereby reduced.

The phase modulator is heated during continuous operation over several hours until a balance is produced between the discharged heat and friction losses. When the balance is reached, the temperature of the phase modulator has stabilised at approximately 80° C. Hybrid ceramic bearings can continuously withstand this high operating temperature. When other bearings are used, temperature control is necessary to carry out long measurements because the bearings would have to be exchanged regularly at an operating temperature of approximately 80° C.

A rotatable axis for positioning the phase modulator can be driven, for example, electromagnetically, via a belt, V-belt, compressed air, air turbine drive or toothed wheels.

In a preferred embodiment, the microscope according to the invention has a temperature control. The service-life of the bearings of the rotation shaft is particularly long if the temperature of the device for rotating the phase modulator remains sufficiently low. However, the establishment of the chemical composition of a sample by means of infrared microspectroscopy can take several hours depending on the sample size and the spectral range which is intended to be examined. Furthermore, there are conceivable high throughput applications, in which infrared microscopes are used over several days and longer in continuous operation. As a result of the continuous rotation of the phase modulator, with high rotation rates the rotation shaft is heated during operation of the microscope by friction and/or electrical losses. Therefore, a temperature control is advantageous. As a result of the temperature control, a fluctuation of the measurement signal of the microscope as a result of temperature fluctuations of the device for rotating the phase modulator is prevented. The measurement accuracy is thereby increased, in particular during longer measurements.

The temperature control can be carried out, for example, via a coupling of the device for rotating the phase modulator to a cooling circuit with water cooling.

As a result of the temperature control, the device for rotating the phase modulator can further be adjusted at a temperature at which no microscope components, in particular no components of the device for rotating the phase modulator, are damaged even during continuous operation. The service-life of the device for rotating the phase modulator is thereby extended and the maintenance complexity of the microscope is thereby reduced.

In a preferred embodiment, the temperature control is carried out by a passive labyrinth air cooling. The purging air used for this purpose preferably corresponds to dried compressed air, as supplied by an FTIR "purge gas" generator. Dried compressed air is thereby supplied to the infrared microscope and is simultaneously advantageous in order to minimise the effects of fluctuating air humidity on the measurement. Nitrogen or oxygen are also suitable as purging air.

In a preferred embodiment, a shaft for positioning the phase modulator and a device for orientating the phase modulator rotate relative to the shaft without any imbalance. This may, for example, be achieved by a rotationally symmetrical construction form. Without an imbalance being avoided, the mechanical loading of the rotating phase modulator on the microscope would be clearly visible. The microscope would begin to oscillate, which becomes evident at high magnifications as shaking of the sample. The optical resolution is thereby reduced. As a result of imbalance being avoided, such undesirable mechanical influences on the measurement with the microscope are minimised. Furthermore, the service-life of the bearings used is increased.

In a preferred embodiment, the microscope does not have any natural frequencies in the range of the rotation frequencies of the phase modulator but instead has vibration-damping properties. The mechanical influences of the rotating phase modulator on the measurement with the microscope can thereby be further reduced.

In a preferred embodiment, a shaft for positioning the phase modulator and a drive shaft of the phase modulator are identical. The construction form of the device for rotating the phase modulator is thereby reduced. In a particularly preferred embodiment, the shaft is a hollow shaft, into the interior of which the infrared radiation extends in order to illuminate the sample in the microscope.

In another aspect, the invention relates to a method for the molecular spectroscopic analysis of a sample comprising the steps of irradiating the sample with an infrared (IR) radiation by means of a quantum cascade laser (QCL), wherein the IR radiation is directed onto the sample via a phase modulator and at least one optical element, and detecting the IR radiation which is reflected and/or transmitted by the sample. The phase modulator is a rotatable IR-transparent scattering plate or a rotatable scattering mirror which reflects IR radiation. By the phase modulator being continuously rotated during the detection and no IR radiation which is scattered at the center of the phase modulator being directed onto the sample, the use of QCL for molecular spectroscopic analyses of complex samples becomes possible. In comparison with conventional methods, high-resolution and precise measurements can be carried out in a very short time. FT-IR measurements which have a similar resolution require from several minutes to hours, whereas analyses with the method according to the invention can already be concluded within a few seconds. Although measurements using QCL in conjunction with rapid MCT-FPAs allow shorter measurement times than FT-IR systems, they have without phase modulation excessively high measurement inaccuracies for a reliable analysis of complex samples (Yeh et al., 2015).

In order to achieve the situation that no IR radiation which is scattered at the center of the phase modulator is directed onto the sample, the method can be adapted in various manners. In a preferred embodiment, the center of the phase modulator is not included by the IR radiation. No IR radiation which is scattered at the center of the phase modulator is thereby produced.

In another embodiment, the IR radiation is directed onto the sample via a cover which is arranged downstream of the center of the phase modulator, wherein the cover blocks the IR radiation which is scattered at the center of the phase modulator.

In another embodiment, the IR radiation is directed onto the sample via a lens arrangement which is arranged between the phase modulator and the sample, wherein the lens arrangement directs only the IR radiation which is scattered outside the center of the phase modulator onto the sample.

In a preferred embodiment, at least 2, preferably from 2 to 10, more preferably from 2 to 6, more preferably from 2 to 4 different wavelengths of the transmitted and/or reflected IR radiation are detected. For the analysis of biological samples, the recording of two different wavelengths may already be sufficient to image the structure of a tissue, in particular the position and the state of the cells. Instead of analysing a complete spectrum, it is possible to record images of a few individual wavelengths, whereby the recording time is significantly reduced. At a frame rate of the sensor of 50 Hz and a recording of 19 images per wavelength, for example, only 2.5 seconds are needed to carry out measurements at two different wavelengths.

In a preferred embodiment, the IR radiation is detected with a spectral resolution of from 1 $cm^{-1}$ to 8 $cm^{-1}$, preferably from 2 $cm^{-1}$ to 8 $cm^{-1}$, more preferably from 4 $cm^{-1}$ to 8 $cm^{-1}$. If a spectrum is intended to be recorded over a plurality of wavelengths, a resolution of from 1 $cm^{-1}$ to 8 $cm^{-1}$ is preferred. A resolution of less than 1 $cm^{-1}$ is generally not possible because the spectral line width of a QCL is at least 0.5 $cm^{-1}$. The line width is consequently the lower limit for the spectral resolution. Depending on the sample, however, a lower resolution may be adequate, whereby the recording speed is increased. For example, biological samples usually do not have, in the IR spectrum, specific properties which require a high resolution. Therefore, a resolution of from 4 $cm^{-1}$ to 8 $cm^{-1}$ is sufficient for biological samples. For a resolution of 4 $cm^{-1}$, a QCL having an interval width of 2 $cm^{-1}$ can be tuned. For a resolution of 8 $cm^{-1}$, an interval width of 4 $cm^{-1}$ is accordingly possible. At a resolution of from 4 $cm^{-1}$ to 8 $cm^{-1}$, a plurality of successive images can further be integrated, whereby the ratio of the signal to the background noise can be substantially improved. Thus, at a resolution of 4 $cm^{-1}$ (that is to say, an interval width of 2 $cm^{-1}$) at a tuning speed of 10 $cm^{-1}$ per second and a frame rate of 50 Hz, 10 images can be integrated, respectively (2 $cm^{-1}$/10 $cm^{-1}$/s*50 Hz=0.2 seconds*50 Hz=10). Accordingly, at a resolution of 8 $cm^{-1}$ (that is to say, an interval width of 4 $cm^{-1}$) and a tuning speed of 10 $cm^{-1}$/s and 50 Hz frame rate, 20 images can be integrated.

In a preferred embodiment, the method further comprises the step of focusing the sample in accordance with the wavelength of the IR radiation of the QCL. The imaging of the sample on the detector is often dependent on the wavelength of the incident light. Since the QCL emits substantially discrete wavelengths, it is possible to adjust the focus of the detector accordingly. During the recording of a spectrum over a plurality of wavelengths by tuning the QCL, the wavelength of the radiation being introduced at the detector changes continuously, whereby the focus may be lost. An adaptation of the focus in accordance with the wavelength of the QCL is consequently advantageous. This can be carried out, for example, by the synchronised displacement of the sample or the detector. In this case, a displacement of the detector is generally simpler to carry out because in the case of magnifications the distance which it has to be displaced is longer in comparison with the sample and there is consequently a higher tolerance for the positioning accuracy. In order to position the detector or the sample in accordance with the wavelength emitted by the QCL, the position thereof can be controlled by means of a computer unit. The computer unit further comprises a wavelength referencing, for example, a phase-dependent interferometer. The information which is introduced by the wavelength referencing in relation to the emitted wavelength is processed by the computer unit and the position of the detector or the sample is adapted accordingly.

In this manner, it is ensured that the sample for each wavelength is sharply imaged on the detector.

In a preferred embodiment, the method further comprises the step of producing a hyperspectral imaging of the sample. The term "hyperspectral imaging" is intended to refer to a pictorial representation of the sample which is based on the measurement of at least two different wavelengths, preferably on a partial or complete IR spectrum of the sample. It reproduces the structure of the sample on the basis of the biochemical composition thereof so that, for example, in the case of a tissue sample the arrangement and the state of the cells and other tissue structures (for example, connective tissue) can be identified.

In a preferred embodiment, the phase modulator rotates at a rate which is at least 5%, preferably at least 8%, more preferably at least 20%, higher than a frame rate of the detector (sensor). The inventors have established that the measurement accuracy can be further increased by the phase modulator continuously rotating at a rate which is at least 5% higher than the frame rate. Generally, therefore, a high level of measurement precision is possible with short measurement times. This is particularly decisive for analyses of biological samples accompanying operations.

EXAMPLES

1. Preferred Embodiments

FIG. 1 shows a first general embodiment of the microscope 1 according to the invention. The microscope 1 comprises two QCLs 3, the laser beams of which are emitted via redirecting mirrors 12 and beam splitters 24 onto a rotating phase modulator 5. Subsequently, the radiation falls through a lens 6 onto a sample 2, which is fixed to a sample holder 8. The IR radiation which is emitted by the sample 2 is detected by a sensor 4. At the same time, a portion of the laser radiation of the QCLs 3 is supplied to a wavelength referencing 7 via a beam splitter 24. The control and verification of the microscope 1 are brought about via a laser control 9, a recording unit 10 and a lock-in amplifier 11.

FIG. 2 shows embodiments of the beam path through the microscope 1 during transmission (FIGS. 2 A to D, I and J) and reflection (FIGS. 2 E to H, K and L), wherein the IR radiation is imaged directly onto the sample. Both a rotating IR-transparent scattering plate 21 (FIG. 2 A to H) and a rotating IR-reflective scattering mirror 25 (FIG. 2 I to L) can be used as a phase modulator. In addition to the rotating phase modulator 5, an additional non-moving scattering plate 23 or scattering mirror 26 which reflects IR (FIGS. 2 B, C, F, H, J and L) can be used. Furthermore, there can be arranged in the beam path different lenses which are used to image the radiation spot of the phase modulator 5 onto the sample (lenses 22), to focus the QCL 3 onto the rotating phase modulator 5 (lens 27) or to focus of the radiation which is emitted by the sample 2 onto the sensor 4 (lenses 28).

Figure 3:
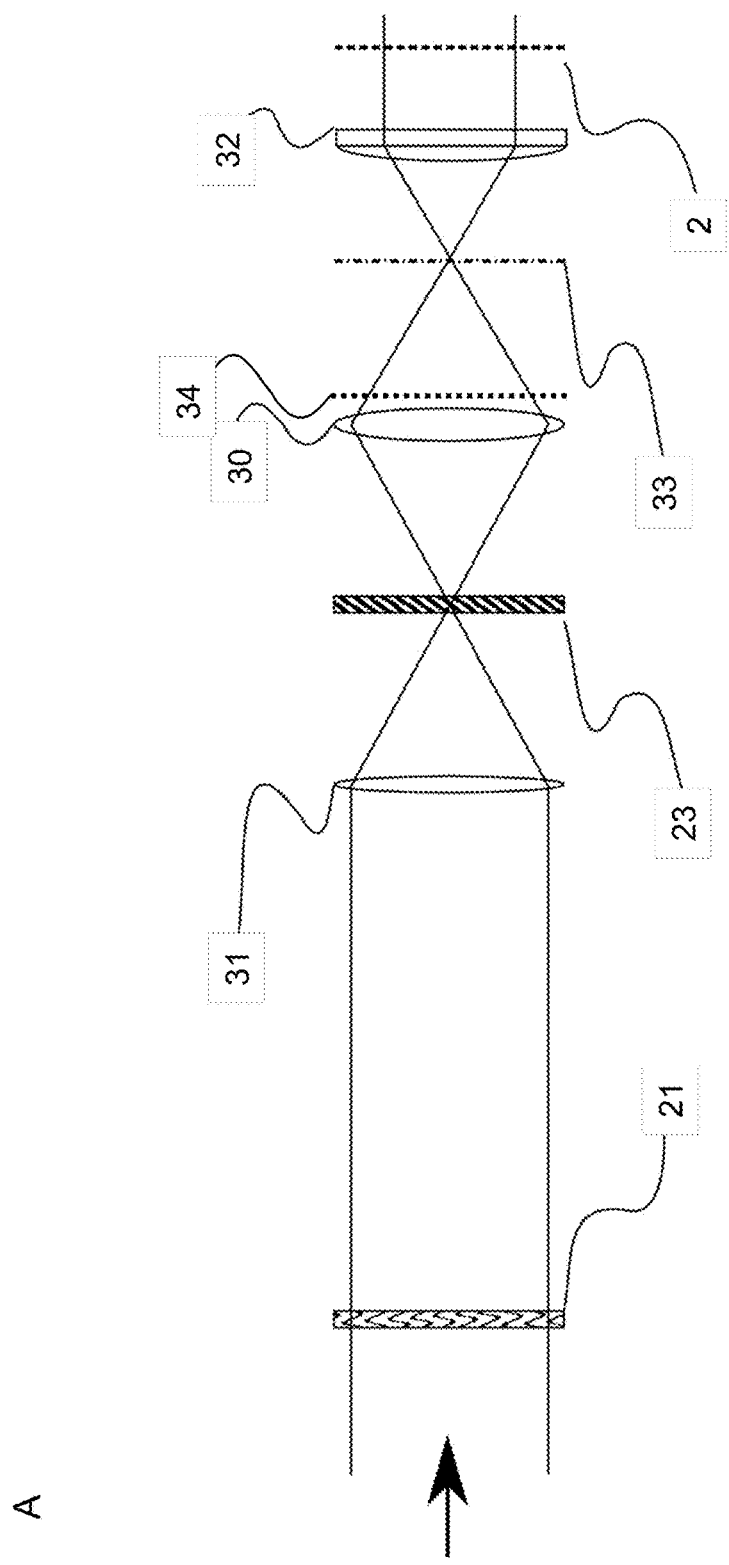
FIG. 3 shows various embodiments of the beam path of an IR microscope according to the invention with single (A) and four-fold (B) magnification. In the embodiment according to depiction A, the IR radiation is imaged onto the aperture diaphragm.
Figure 3:
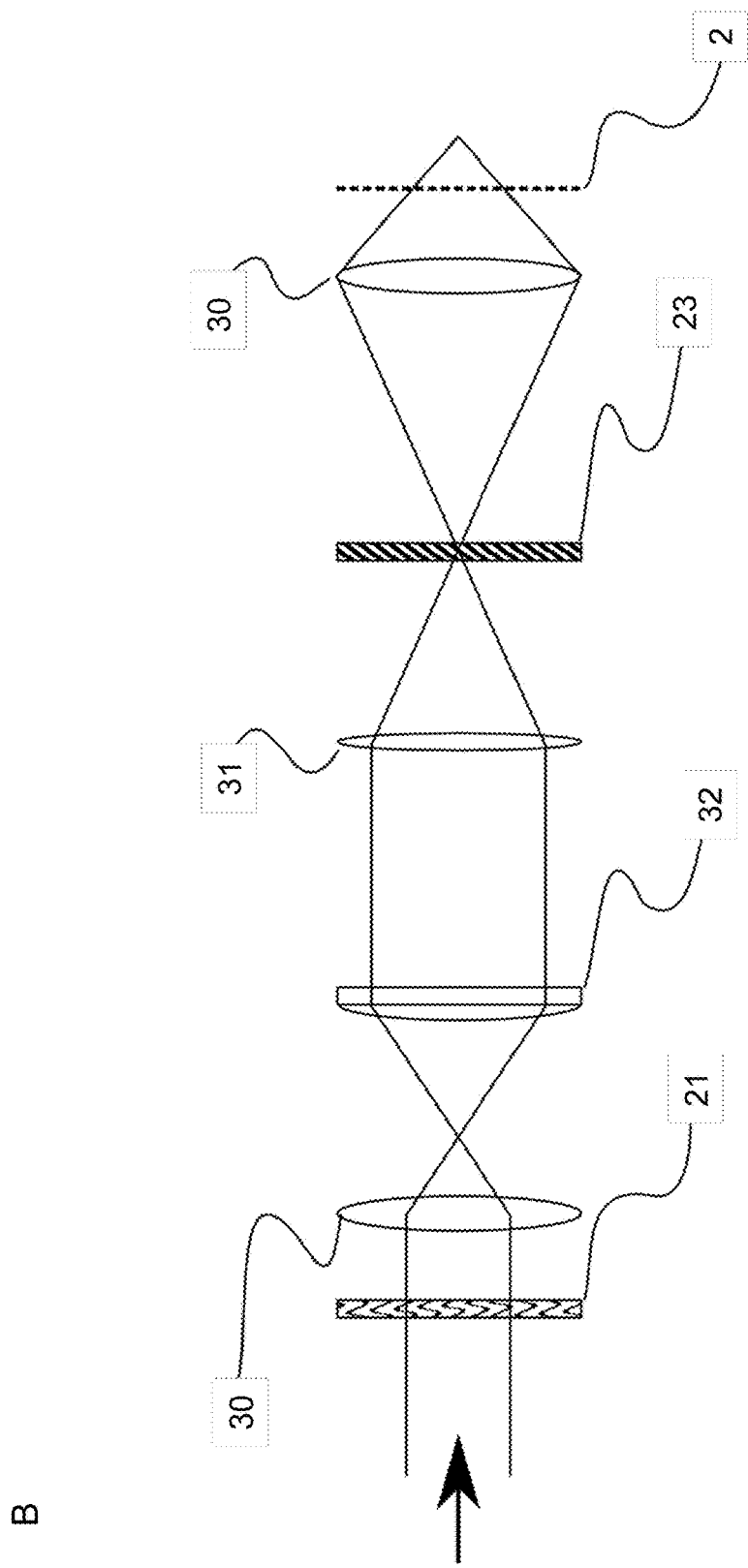

FIG. 3 shows two embodiments of the beam path through the microscope 1 during transmission. According to FIG. 3 A, the IR radiation is imaged by the rotating IR-transparent scattering plate 21 via a zinc selenide lens (f=50 mm) 31, a non-moving IR-transparent scattering lens 23 and a collector lens (zinc selenide, f=25 mm) 30 onto the aperture diaphragm 33. This arrangement corresponds to a Köhler illumination which produced in particular an extraordinarily homogeneous and interference-free image with a single magnification. FIG. 3 B shows a construction for a four-fold magnification. In this instance, the IR radiation is directed onto a non-moving IR-transparent scattering lens 23 by the rotating IR-transparent scattering plate 21 via a zinc selenide lens (f=25 mm) 30, a capacitor lens (barium fluoride, f=30/22.8 mm) 32 and a zinc selenide lens (f=50 mm) 31. From this lens 23, the IR radiation is imaged downstream of the sample 2 by means of a zinc selenide lens (f=25 mm) 30.

2. Configuration of the Phase Modulator

In order to establish the configuration of the phase modulator, referencing operations of two blank measurements were carried out, wherein the rotation rate and the illumination of the scattering plate were varied. All the measurements were carried out with a QCL with a spectral range of from 1027 to 1087 $cm^{-1}$. The optical construction of the illumination is illustrated in FIG. 3 B. Both scattering plates had a diameter of 25.4 mm. The diameter of the laser beam was approximately 10 mm. For each blank measurement, the QCL was tuned three times in approximately 11 seconds from 1027 to 1087 $cm^{-1}$. The detection was carried out at an imaging scale of 4:1 with an effective pixel size of 3.65 μm. The microbolometer camera operated at a frame rate of 50 Hz.

After referencing the first blank measurement onto the second blank measurement, in each pixel the spectral standard deviation of the absorption spectrum can be calculated. This characteristic variable was introduced in order to evaluate the measurement accuracy by Phillips et al., 2013. The absorbance is in this case defined as the negative natural logarithm of the relative transmission. The spectral standard deviation is calculated pixel by pixel from the referencing of a first blank measurement onto another blank measurement and can be interpreted as a width of the 0 absorbance line in each pixel. Initially, a measurement was carried out with the configuration shown in FIG. 3 B, wherein the center of rotation of the moving scattering plate was illuminated by the laser and was imaged in the viewing field of the detector (experiments 1 and 2). For experiments 3 and 4, the moving scattering plate was displaced by several millimeters so that the center of the moving scattering plate was not illuminated. In order to evaluate the four experiments, the data were averaged with a spectral interval width of an average of 2.4 $cm^{-1}$.

Spectral Standard Deviation with Different Rotation Rates and Illumination:

| Experiment | Rotation rate | Illumination of the center | Mean value of the spectral standard deviation [a.u.] |
|---|---|---|---|
| 1 | 51 Hz | + | 0.0227 |
| 2 | 60 Hz | + | 0.0081 |

| Experiment | Rotation rate | Illumination of the center | Mean value of the spectral standard deviation [a.u.] |
|---|---|---|---|
| 3 | 51 Hz | – | 0.0172 |
| 4 | 60 Hz | – | 0.0054 |

Experiments 1 to 4 show that the spectral standard deviation is significantly reduced if the center of the scattering plate is not included by the laser beam and consequently is also not imaged in the viewing field of the detector.

Furthermore, the measurement accuracy is significantly increased if a rotation rate which is 20% higher than the frame rate of the detector (here a rotation rate of 60 Hz at a frame rate of the microbolometer camera of 50 Hz) is selected for the moving scattering plate.

Experiments 5-9 were carried out with an improved optical illumination unit, through which more light strikes the detector. A higher signal could thereby be reached so that the ratio of signal to background noise is improved. The fact that more light strikes the detector was achieved in that the laser beam was not widened unlike the experiments 1-4. Alternatively, a laser having a smaller beam diameter or a smaller étendue can be used. The étendue measures the extent of a beam bundle. It comprises the cross-section and the spatial angle and does not change when a beam bundle passes through an optical system.

Figure 6:
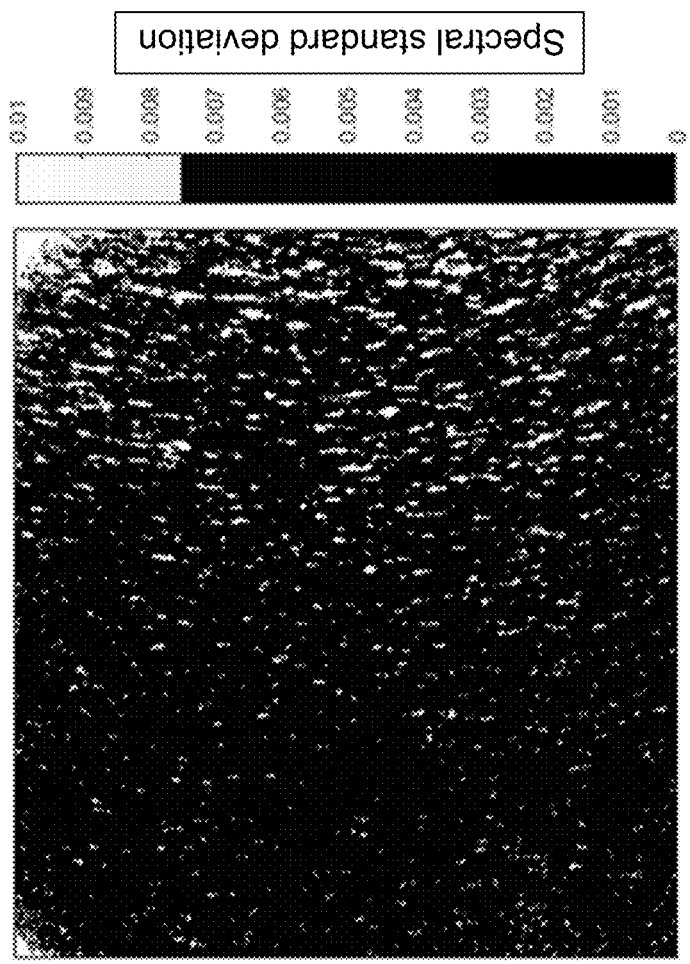
FIG. 6 shows the spectral standard deviation calculated pixel by pixel (calculated using the natural logarithm) from experiment 5.

In experiment 5, the measurement accuracy was calculated by referencing the mean hyperspectral image comprising 5 blank measurements over the spectral range of from 1027 to 1087 cm$^{-1}$ onto the mean hyperspectral image of 5 additional blank measurements over the identical spectral range. The rotation rate of the moving scattering plate was 62.5 Hz. The frame rate of the detector was 50 Hz. FIG. 6 illustrates the spectral standard deviation which is calculated pixel by pixel (calculated using the natural logarithm). The center or the center of rotation of the scattering plate is on the right outside the field of the image. Consequently, the path speed at the left-hand image edge is highest and at the right-hand image edge lowest. The increase of the white regions from the left image edge to the right image edge indicates that the measurement accuracy increases in the direction towards the right-hand image edge. This means that the measurement accuracy increases the closer the IR radiation strikes to the center of rotation of the scattering plate. Consequently, with a greater spacing from the center of the scattering plate, a higher measurement accuracy is achieved than with a smaller spacing from the center of the scattering plate. The position of the center of rotation or the center of the scattering plate to the right outside the image field is indicated by annular structures in FIG. 6.

Figure 7:
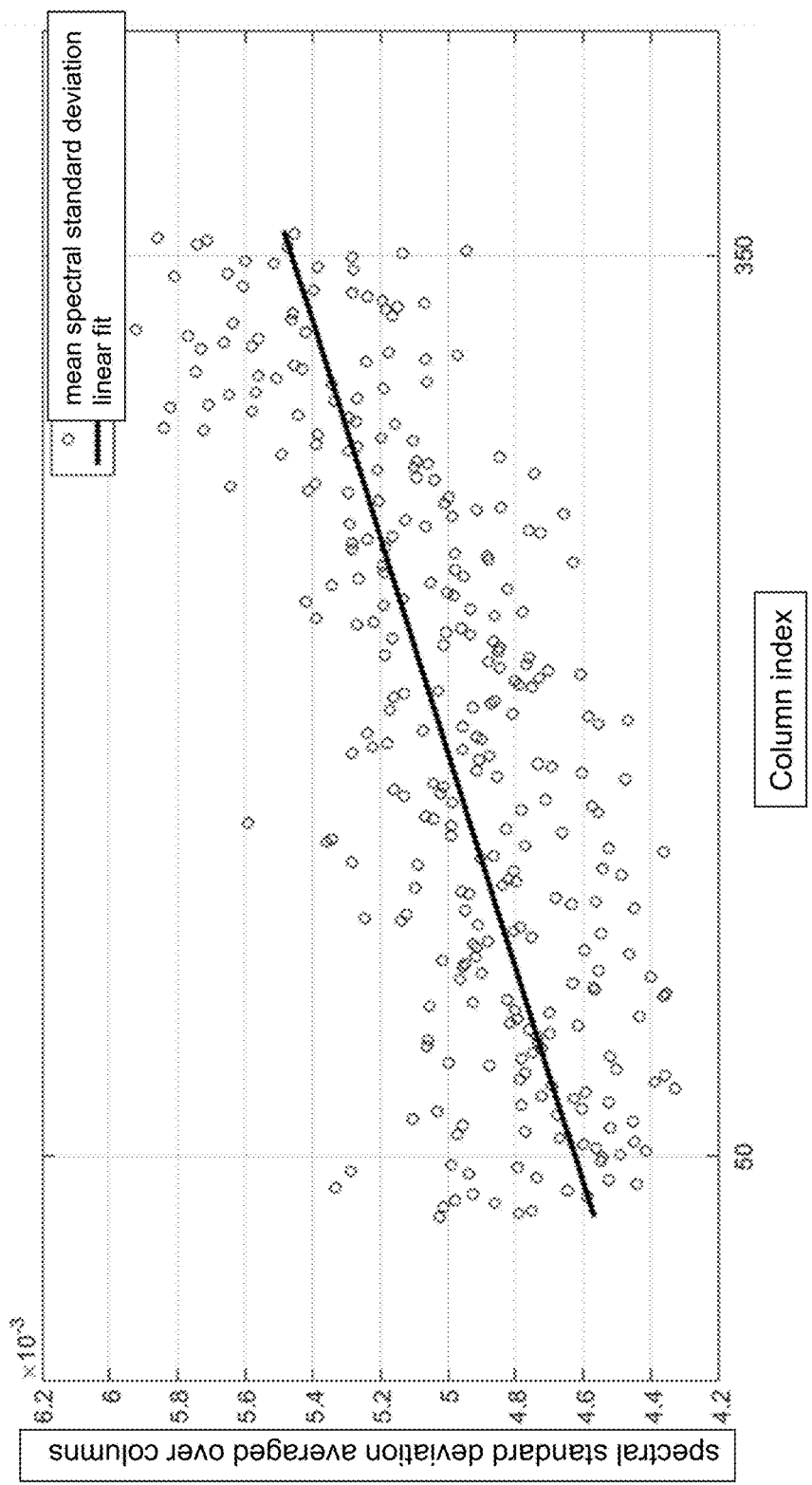
FIG. 7 shows the relationship between the spectral standard deviation and the column index from FIG. 6.

The image of FIG. 6 was subdivided into columns. Each column has a width of 7.3 µm. The column index was fixed in an increasing manner from left to right. Since the center of rotation of the scattering plate is to the right outside the image field, a smaller column index corresponds to a greater spacing with respect to the center of rotation of the scattering plate and therefore a higher path speed. By means of averaging over the columns of the image, an approximately linear relationship between the measurement accuracy and the column index was obtained (FIG. 7). In FIG. 7, 200 columns were assumed (corresponds to 1.46 mm) for the spacing of the center of the rotation plate with respect to the right image edge. A fit with a linear function resulted in the following fit parameters:

$y=b1*(2*\pi*7.3 \mu m*((350-x)+b2)*62.5 Hz+b3$     Function:

where
y is the mean spectral standard deviation [a.u.],
x is the column index,
b1 is the proportionality constant between the path speed and mean spectral standard deviation [a.u./(m/s)],
b2 is the spacing of the center of the scattering plate from the right-hand image edge and
b3 is the path-speed-independent proportion of the mean spectral standard deviation [a.u.].

For the spacing of the center of the rotation plate from the right-hand image edge, 200 or 1000 columns were assumed (corresponds to 1.46 and 7.3 mm), wherein a column corresponds to a spacing of 7.3 µm.

| b2 | 200 (corresponds to 1.46 mm) | 1000 (corresponds to 7.3 mm) |
|---|---|---|
| b1 [a.u./(m/s)] | −0.0010646 | −0.0010646 |
| b3 [a.u.] | 4.4495*10$^{-5}$ | 6.2318*10$^{-5}$ |

The image field in FIG. 6 has a width of approximately 3 mm. The mean spectral standard deviation at the left-hand image edge is substantially lower than at the right-hand image edge, which results from the 3 mm greater spacing from the center of the scattering plate. Consequently, the results show that the highest measurement accuracy is achieved by the IR radiation striking the scattering plate with the greatest possible spacing from the center of the scattering plate.

Experiments 6-9 were carried out with the same parameters as experiment 5 except that 3 were referenced with respect to 3 blank measurements and the center of rotation was further removed from the image. The rotation rate was varied in order to examine the influence of the rotation rate on the measurement accuracy.

Spectral Standard Deviation with Different Rotation Rate and Illumination:

| Experiment | Rotation rate | Illumination of the center | Mean value of the spectral standard deviation [a.u.] |
|---|---|---|---|
| 5 | 62.5 Hz | + | 0.0052 |
| 6 | 54 Hz | – | 0.0028 |
| 7 | 58 Hz | – | 0.0019 |
| 8 | 64 Hz | – | 0.0019 |
| 9 | 70 Hz | – | 0.0017 |

Experiment 6 shows that, when the moving scattering plate rotates at a rotation rate which is 8% greater than the frame rate of the detector (here, a rotation rate of 54 Hz at a frame rate of the microbolometer camera of 50 Hz), a very high level of measurement accuracy is achieved. Experiments 6-9 show that the measurement accuracy further increases with an increasing rotation rate of the scattering plate.

Figure 4:
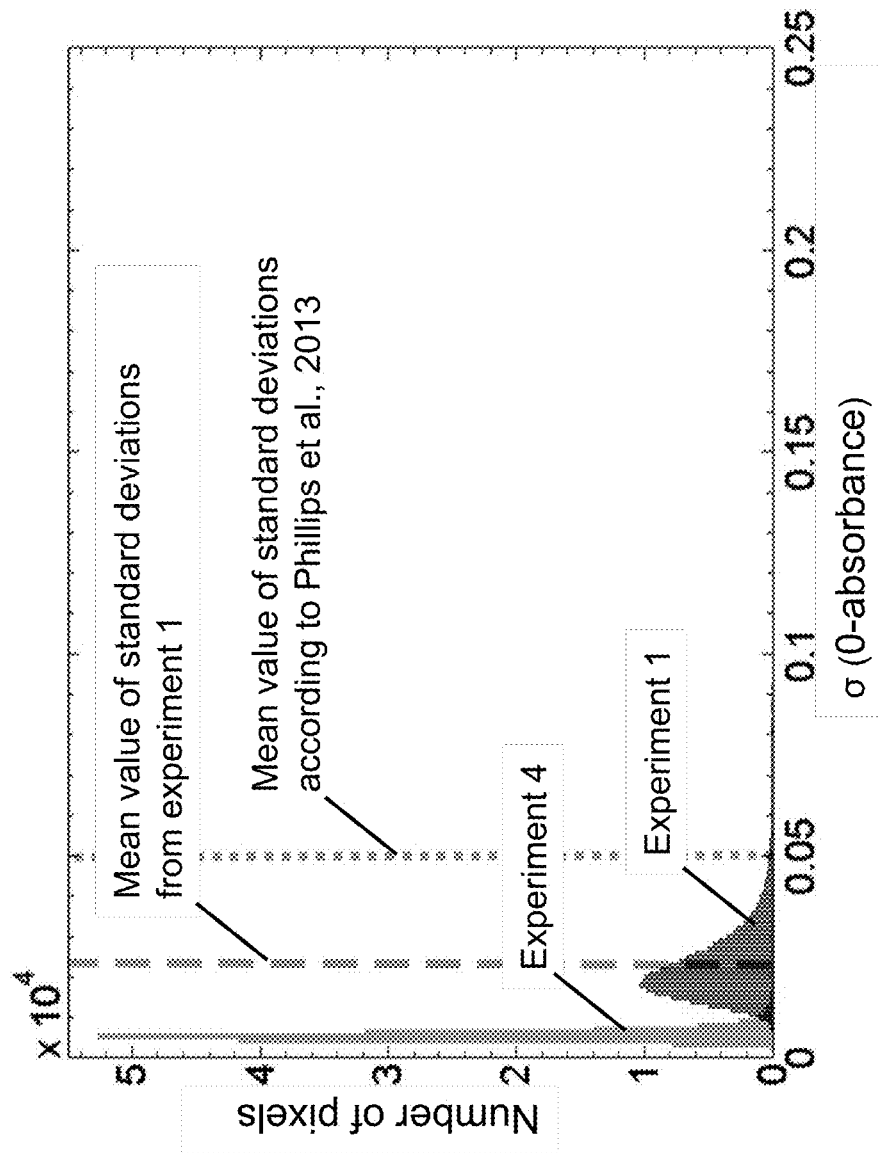
FIG. 4 shows the distribution of the spectral standard deviation of the 0 absorbance line which is calculated pixel by pixel from experiments 1 and 4. For comparison, the mean value of the standard deviations of all the pixels from Phillips et al., 2013 is shown.

FIG. 4 shows a histogram of the spectral standard deviation which is calculated pixel by pixel for experiments 1 and 4. The spectral standard deviation was in both experiments substantially below the conventional methods (Phillips et al., 2013). This shows that the measurement accuracy is substantially improved by reducing the spatial coherence over the averaged time.

Another method for establishing the measurement error was proposed recently by Yeh at al., 2015. In this case, the quadratic mean of the pixel values is calculated from an image with a fixed wavelength. Since Yeh et al., 2015 define the absorbance via the decimal logarithm, this definition is assumed in this section for better comparability of the results. In Yeh et al., 2015, a nitrogen-cooled MCT detector was used for detection. These detectors are substantially more expensive than microbolometer cameras but have substantially more rapid image recording rates. A reduction of the spatial coherence over the averaged time was dispensed with. This led to considerable fluctuations in the 0 absorbance line of a randomly selected pixel from the QCL measurement in comparison with the fluctuations of the mean of the 0 absorbance lines of 1000 pixels (Yeh et al., 2015). This divergence shows that a systematic measurement error is present in QCL-based measurements.

Figure 5:
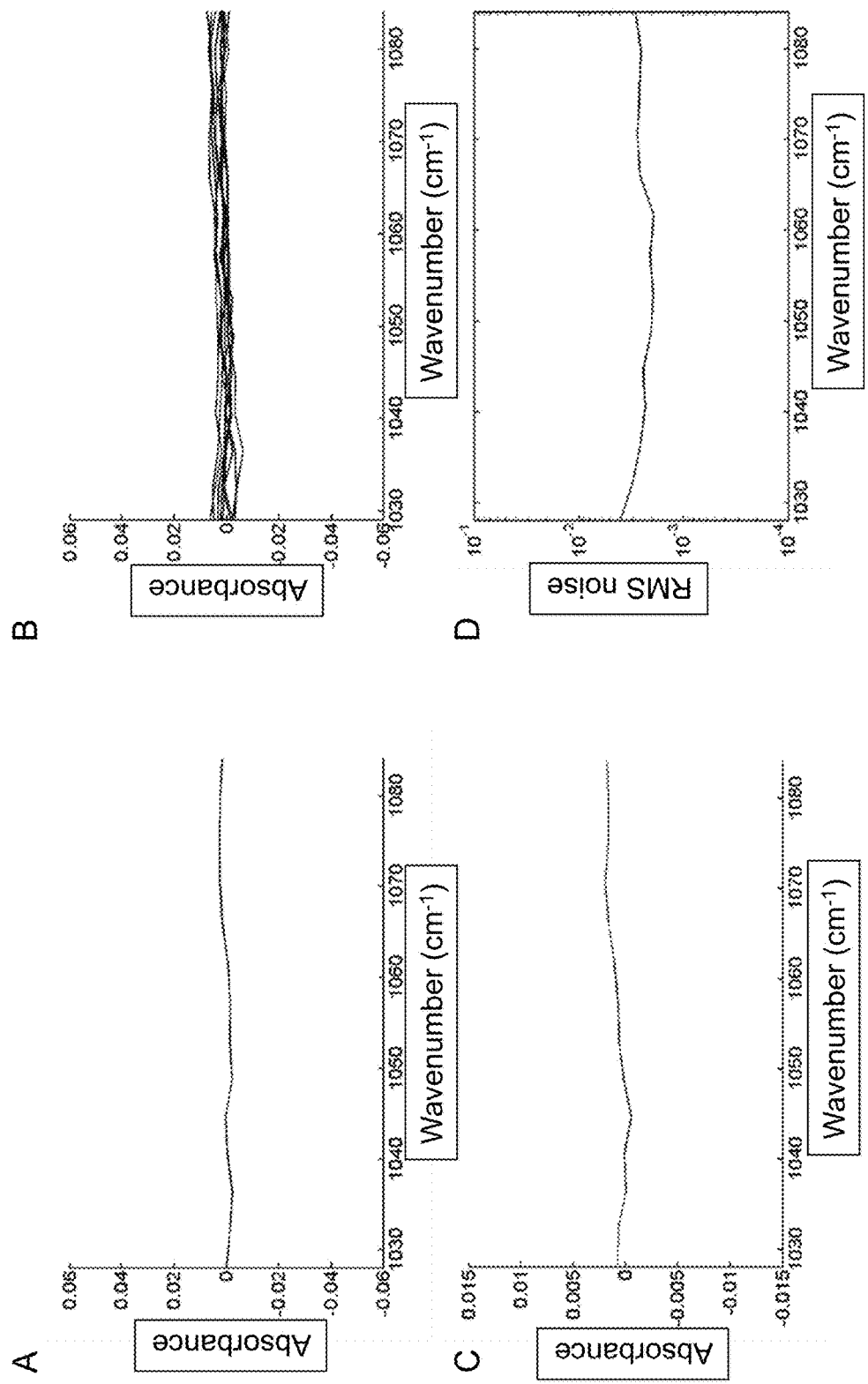
FIG. 5 shows the 0 absorbance line of a randomly selected pixel (A), 10 randomly selected pixels (B), the mean value of 1000 0 absorbance lines (C) and the spatial, quadratic mean value calculated for the data (D) from experiment 4.

Unlike the microscopic structure described in Yeh et al., 2015, the 0 absorbance line in experiment 4 is also near the absolute 0 line when individual pixels are observed (FIG. 5). There are no apparently periodic fluctuations about the 0 line. In addition, the accuracy, that is to say, the spacing of the measured 0 absorbance line from the absolute 0 line, is smaller in experiment 4 than in all the cases considered in Yeh et al., 2015. This is particularly noticeable when a microbolometer was used in experiment 4 for detection, the recording quality of which is in principle significantly less than that of MCT-FPAs. The spatial coherence of the QCL accordingly leads to systematic measurement errors which cannot be readily corrected even by using highly sensitive and expensive MCT-FPAs. However, the system used in experiment 4 for the QCL-based microscopy with a microbolometer camera can minimise these measurement errors by using the scattering plates to reduce the spatial coherence over the averaged time. The measurement accuracy obtained in this manner is comparable with FTIR-based systems with a substantially reduced measurement time.

3. Identification of Beaker Cells in Non-Dyed Thin Sections of the Large Intestine 3.1 Equipment and Methods Samples of the large intestine were removed from healthy adult C57BL/6 mice and fixed. 8 µm thick paraffin sections were produced from the tissue and examined by means of IR microscopy.

To this end, there were used two quantum cascade lasers (Daylight Solutions Inc., USA) which could be tuned over 1027 to 1087 cm$^{-1}$ and 1167 to 1319 cm$^{-1}$ (corresponds to a wavelength range of 9.74 µm to 9.20 µm and 8.57 µm to 7.58 µm). For the measurement, each laser was tuned over the entire range twenty times within 11.3 seconds. A microbolometer array comprising 640×480 pixels (InfraTec GmbH, Germany) was used to detect the IR radiation which is transmitted by the sample. The frame rate was 50 Hz. The rotation rate of the scattering plate was higher than the frame rate of the microbolometer. All the measurements were recorded with a projected center distance of the pixels ("Projected Pixel Pitch") in the sample plane of 3.65 µm. Two infrared lenses were used for a 4:1 magnification and the viewing field was 2.8×3.1 mm$^2$. The local resolution was 9.4±1.8 µm (at 1065 cm$^{-1}$).

The synchronisation of the tuning time and the frame rate of the bolometer result in a spectral resolution of 4 cm$^{-1}$ which is sufficient for the analysis of the middle infrared spectrum of thin tissue sections. The absolute recording time for IR images over the complete tuning width of the lasers was 7.5 minutes for each of the six samples examined. A single blank measurement was recorded during an additional time of 1.9 minutes which was used as a reference for all six hyperspectral imagings. The absorption spectrums were calculated as negative natural logarithms of the transmission spectrums for each pixel individually. Except for a background correction, averaging over spectral ranges (spectral binning) (at a mean range width of 2.4 cm$^{-1}$), a water absorption correction and a Gaussian blur filter, no additional pre-processing operations were carried out.

In order to analyse the mean IR spectral information, four steps were carried out:

1. random selection of one of six thin sections which was used as a so-called training sample,
2. non-monitored classification of the sample data with exclusive use of the information of the training sample. k-means-algorithm was applied to the training data and a total of ten groups were selected, of which three were associated with the paraffin spectrum or the blank substrate and seven with the tissue. In total, 323,300 individual spectrums were used to train the classification method.
3. Training of a classification method (random decision forest) on the basis of step 2, wherein only the training sample was used. In total, 100 decision trees were developed.
4. After steps 1 to 3, no additional trainings ("retraining") or changes can be accepted. The trained classification method was subsequently applied to the remaining thin sections ("blind validation") and used as the result of the analysis.

All analyses were carried out using MATLAB (R2014a, The MathWorks Inc., USA).

3.2 Results

The analysis of a single wavelength was already sufficient to obtain a first impression of the quality of the imaging obtained. The recording of the infrared transmission at 1218 cm$^{-1}$ (±1.2 cm$^{-1}$) over the complete large intestine section clearly showed the central lumen surrounded by large intestine epithelium and muscle tissue (Lamina muscularis mucosae). By digital zoom, the substructure of the epithelium could also be identified. Despite the astonishingly extensive information which could already be obtained from the recordings of a single wavelength, complete spectrums according to step 2 of the data analysis (k-means) were used for the additional examinations. The IR images obtained clearly showed the morphology of the tissue, with the mucus layer which is located inside the large intestine. This contains in particular mucin which is produced by beaker cells and as a result of the high proportion of highly glycosylated peptides has a high IR absorption in the carbohydrate range (from 1000 to 1100 cm$^{-1}$). In order to associate each pixel of the hyperspectral recording with a specific tissue, the ratio of the absorbance was calculated at 1079 cm$^{-1}$ and 1181 cm$^{-1}$ and the absorbance integral from 1027 cm$^{-1}$ to 1087 cm$^{-1}$ (Table 1). Thus, not only the mucus layer and beaker cells but also Lamina muscularis, the Lamina propria and the epithelium cells surrounding beaker cells were able to be identified.

TABLE 1

| Biomedical association | Absorbance ratio 1079 cm$^{-1}$/1181 cm$^{-1}$ [random unit] Mean value −Δq0.05, +Δq0.95 | Absorbance integral 1027 cm$^{-1}$ to 1087 cm$^{-1}$ [random unit] |
|---|---|---|
| Mucin/Beaker cells | 3.01−1.48, +7.27 | 8.42 −2.24, +2.18 |
| Lamina muscularis, lamina propria, colon enterocytes | 1.11 −0.47, +0.85 | 3.4 −1.20, +1.63 |
| Lamina propria | 1.33 −0.60, +0.71 | 5.90 −1.86, +1.70 |

TABLE 1-continued

| Biomedical association | Absorbance ratio 1079 cm$^{-1}$/1181 cm$^{-1}$ [random unit] Mean value −Δq0.05, +Δq0.95 | Absorbance integral 1027 cm$^{-1}$ to 1087 cm$^{-1}$ [random unit] |
|---|---|---|
| Colon epithelium cells | 1.47 −0.60, +0.82 | 8.40 −1.88, +2.59 |
| Colon epithelium cells, epithelium cells in the environment of the beaker cells | 1.13 −0.42, +0.57 | 10.32 −2.95, +3.46 |
| Mucus layer in lumen | 1.12 −0.30, +0.41 | 21.04 −5.03, +10.96 |
| Mucus layer in lumen | 1.07 −0.34, +0.48 | 14.38 −3.95, +4.81 |

REFERENCES

M. C. Phillips and B. E. Bernacki, Hyperspectral microscopy of explosive particles using an external cavity quantum cascade laser, Opt. Eng. 52, 2013, 061302

K. Yeh, S. Kenkel, J.-N. Liu and R. Bhargava, Fast Infrared Chemical Imaging with a Quantum Cascade Laser, Anal. Chem. 87, 2015, pp. 485-493

LIST OF REFERENCE NUMERALS

1 Microscope
2 Sample
3 QCL
4 Sensor
5 Phase modulator
6 Optical element
7 Wavelength referencing
8 Sample holder
9 Laser control
10 Recording unit
11 Lock-in amplifier
12 Redirecting mirror
20 Microbolometer FPA
21 IR-transparent scattering plate (moving)
22 Lens for imaging the phase modulator on the sample
23 IR-transparent scattering lens (non-moving)
24 Beam splitter
25 IR-reflective scattering mirror (moving)
26 IR-reflective scattering mirror (non-moving)
27 Lens for focusing the QCL radiation on the rotating phase modulator
28 Lens for focusing the radiation being emitted by the sample onto the detector
29 Laser radiation
30 Collector lens (zinc selenide, f=25 mm)
31 Zinc selenide lens (f=50 mm)
32 Capacitor lens (barium fluoride f=30/22.8 mm)
33 Aperture diaphragm
34 Illumination field diaphragm

The invention claimed is:

1. A microscope for the molecular spectroscopic analysis of a sample having a beam path, the beam path comprising:
at least one quantum cascade laser (QCL) which emits an infrared (IR) radiation;
a phase modulator having a centre, the phase modulator arranged between the QCL and the sample;
at least one optical element which is arranged between the phase modulator and the sample; and
a sensor which detects an IR radiation which is transmitted and/or reflected by the sample,
wherein the phase modulator is a rotatable IR-transparent scattering plate or a rotatable scattering mirror which reflects IR radiation, wherein the phase modulator rotates continuously during the analysis and is arranged in the beam path of the microscope in such a manner that no IR radiation which is scattered at the centre of the phase modulator strikes the sample.

2. The microscope according to claim 1, wherein the phase modulator is arranged in the beam path of the microscope in such a manner that the centre of the phase modulator is not captured by the IR radiation.

3. The microscope according to claim 1, wherein the QCL is a QCL in an external cavity (EC-QCL).

4. The microscope according to claim 1, wherein the QCL is continuously tuned during the analysis.

5. The microscope according to claim 1, wherein the QCL is tuned during the analysis at a speed of from 5 cm$^{-1}$/s to 30 cm$^{-1}$/s.

6. The microscope according to claim 1, wherein the sensor is a thermal sensor.

7. The microscope according to claim 1, wherein the phase modulator rotates at a rate which is at least 5% higher than a frame rate of the sensor (4).

8. The microscope according to claim 1, further comprising a second static phase modulator.

9. A method for the molecular spectroscopic analysis of a sample comprising the steps of
irradiating the sample with an infrared (IR) radiation by means of a quantum cascade laser (QCL), wherein the IR radiation is directed onto the sample via a phase modulator having a centre and at least one optical element; and
detecting the IR radiation which is reflected and/or transmitted by the sample, wherein the phase modulator is a rotatable IR-transparent scattering plate or a rotatable scattering mirror which reflects IR radiation, wherein the phase modulator is rotated continuously during the detection and no IR radiation which is scattered at the centre of the phase modulator is directed onto the sample.

10. The method according to claim 9, wherein the centre of the phase modulator is not captured by the IR radiation.

11. The method according to claim 9, wherein at least 2 different wavelengths of the transmitted and/or reflected IR radiation are detected.

12. The method according to claim 9 or, wherein the IR radiation is detected with a spectral resolution of from 1 cm$^{-1}$ to 8 cm$^{-1}$.

13. The microscope according to claim 1, wherein the QCL is tuned during the analysis at a speed of from 10 cm$^{-1}$/s to 20 cm$^{-1}$/s.

14. The microscope according to claim 1, wherein the QCL is tuned during the analysis at a speed of approximately 10 cm$^{-1}$/s.

15. The microscope according to claim 6, wherein the thermal sensor is a microbolometer.

16. The microscope according to claim 1, wherein the phase modulator rotates at a rate that is at least 8% higher than a frame rate of the sensor.

17. The microscope according to claim 1, wherein the phase modulator rotates at a rate that is at least 20% higher than a frame rate of the sensor.

18. The method according to claim 9, wherein from 2 to 10 different wavelengths of the transmitted and/or reflected IR radiation are detected.

19. The method according to claim 9, wherein from 2 to 6 different wavelengths of the transmitted and/or reflected IR radiation are detected.

20. The method according to claim 9, wherein from 2 to 4 different wavelengths of the transmitted and/or reflected IR radiation are detected.

21. The method according to claim 9, wherein the IR radiation is detected with a spectral resolution of from 2 cm$^{-1}$ to 8 cm$^{-1}$.

22. The method according to claim 9, wherein the IR radiation is detected with a spectral resolution of from 4 cm$^{-1}$ to 8 cm$^{-1}$.

* * * * *